(12) United States Patent
Leksic et al.

(10) Patent No.: US 10,689,352 B2
(45) Date of Patent: Jun. 23, 2020

(54) SOLID STATE FORMS OF TRISODIUM VALSARTAN: SACUBITRIL

(71) Applicant: Teva Pharmaceuticals International GMBH, Jona (CH)

(72) Inventors: Edislav Leksic, Zagreb (HR); Dijana Skalec Samec, Zagreb (HR); Damir Sahnic, Zagreb (HR); Dejan Kisicek, Klenovnik (HR); Martina Hrkovac, Zagreb (HR); Edi Topic, Malinska (HR)

(73) Assignee: TEVA PHARMACEUTICALS INTERNATIONAL GMBH, Jona (CH)

( * ) Notice: Subject to any disclaimer, the term of this patent is extended or adjusted under 35 U.S.C. 154(b) by 0 days.

(21) Appl. No.: 15/735,717

(22) PCT Filed: Jun. 10, 2016

(86) PCT No.: PCT/US2016/036905
§ 371 (c)(1),
(2) Date: Dec. 12, 2017

(87) PCT Pub. No.: WO2016/201238
PCT Pub. Date: Dec. 15, 2016

(65) Prior Publication Data
US 2018/0155300 A1    Jun. 7, 2018

Related U.S. Application Data

(60) Provisional application No. 62/174,938, filed on Jun. 12, 2015, provisional application No. 62/212,817, filed on Sep. 1, 2015, provisional application No. 62/311,070, filed on Mar. 21, 2016.

(51) Int. Cl.
| | | |
|---|---|---|
| C07D 257/04 | (2006.01) | |
| C07C 233/47 | (2006.01) | |
| A61P 9/12 | (2006.01) | |
| A61P 9/04 | (2006.01) | |
| C07C 231/24 | (2006.01) | |

(52) U.S. Cl.
CPC ............ *C07D 257/04* (2013.01); *A61P 9/04* (2018.01); *A61P 9/12* (2018.01); *C07C 231/24* (2013.01); *C07C 233/47* (2013.01); *C07B 2200/07* (2013.01); *C07B 2200/13* (2013.01)

(58) Field of Classification Search
CPC .................................................. C07D 257/04
See application file for complete search history.

(56) References Cited

U.S. PATENT DOCUMENTS 5,217,996 A * 6/1993 Ksander ............... C07C 233/47
                                                                514/533
8,877,938 B2   11/2014 Feng et al.
9,957,240 B2    5/2018 Chen et al.
2018/0201589 A1 7/2018 Chen et al.

FOREIGN PATENT DOCUMENTS

CN    105037289 A    11/2015
WO    2016049663 A1   3/2016

OTHER PUBLICATIONS

Kakkar et al. Drug Development and Industrial Pharmacy, 23(11) p. 1063-1067 (Year: 1997).*
Chauhan et al. IJPI, vol. 2 Issue 4, pp. 37-47. (Year: 2012).*
Caira, Mino R.; "Crystalline Polymorphism of Organic Compounds"; Topics in Current Chemistry, Vol. 198, 1998, pp. 163-208.
International Search Report for International Application No. PCT/US2016/036905, International Filing Date Jun. 10, 2016, dated Aug. 22, 2016, 5 pages.
Written Opinion for International Application No. PCT/US2016/036905, International Filing Date Jun. 10, 2016, dated Aug. 22, 2016, 8 pages.
Third Party Observation for EP3307720A1 (16731747.8), submitted on Apr. 13, 2020, 112 pages.

* cited by examiner

*Primary Examiner* — Emily A Bernhardt
(74) *Attorney, Agent, or Firm* — Cantor Colburn LLP

(57) ABSTRACT

Solid state forms of trisodium vaisartan:sacubitril, processes for their preparation, pharmaceutical compositions containing such solid state forms and treatment methods using the pharmaceutical compositions are described.

22 Claims, 14 Drawing Sheets

PEAKS OF FORM II (cm$^{-1}$) :
700, 742, 763, 819, 862, 907, 942, 1010, 1085, 1176, 1265, 1297, 1357, 1404, 1459, 1488, 1600, 1640, 1716, 2960 cm-1.

TABLE 1 - FULL XRPD PEAK LIST OF CRYSTALLINE
TRISODIUM VALSARTAN:SACUBITRIL FORM II

| XRPD PEAKS (DEGREES TWO THETA) |
| --- |
| 4.3 |
| 5.0 |
| 5.5 |
| 5.8 |
| 7.3 |
| 8.5 |
| 8.9 |
| 9.4 |
| 10.0 |
| 10.9 |
| 11.6 |
| 12.9 |
| 13.7 |
| 13.9 |
| 14.7 |
| 14.8 |
| 15.1 |
| 15.3 |
| 15.9 |
| 16.5 |
| 17.3 |
| 17.6 |
| 18.6 |
| 19.1 |
| 19.5 |
| 20.3 |
| 21.2 |
| 21.9 |
| 23.1 |

FIG. 10

TABLE 2 - PEAK LIST OF FORM II (TWO THETA VALUES) AND
CORRESPONDING D-SPACING VALUES AS CALCULATED BY HIGHSCORE

| DEGREES TWO THETA | CALCULATED D-SPACING, Å |
|---|---|
| 4.3 | 20,341 |
| 5.8 | 15,261 |
| 7.3 | 12,068 |
| 9.4 | 9,397 |
| 10.0 | 8,826 |
| 10.9 | 8,092 |
| 12.9 | 6,863 |
| 14.7 | 6,024 |
| 15.9 | 5,583 |
| 16.5 | 5,353 |
| 18.6 | 4,773 |

FIG. 11

SOLID STATE FORMS OF TRISODIUM VALSARTAN: SACUBITRIL

CROSS REFERENCE TO RELATED APPLICATIONS

This application is a National Stage application of PCT/US2016/036905, filed 10 Jun. 2016, which is related to, and claims the benefit of priority of, U.S. Provisional Application No. 62/174,938 filed on 12 Jun. 2015, U.S. Provisional Application No. 62/212,817 filed on 1 Sep. 2015, and U.S. Provisional Application No. 62/311,070 filed on 21 Mar. 2016, all of which are entitled SOLID STATE FORMS OF TRISODIUM VALSARTAN:SACUBITRIL, the contents of which are incorporated herein by reference in their entirety for all purposes.

FIELD OF THE INVENTION

The present invention encompasses solid state form of trisodium valsartan:sacubitril and processes for its preparation

BACKGROUND OF THE INVENTION

Valsartan:sacubitril (codenamed LCZ696) is a combination drug consisting of two antihypertensive (blood pressure lowering drugs), valsartan and sacubitril.

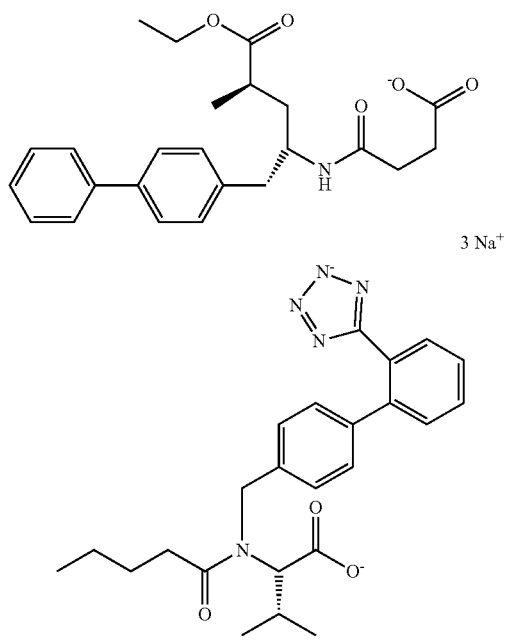

The combination is often described as a dual-acting compounds of angiotensin receptor blockers (ARB) and neutral endopeptidase inhibitors (NEPi). Valsartan is described in U.S. Pat. No. 5,399,578 and Sacubitril in U.S. Pat. No. 5,217,996. U.S. Pat. No. 8,877,938 describes complex of trisodium valsartan-sacubitril hemipentahydrate in crystalline form.

Polymorphism, the occurrence of different crystalline forms, is a property of some molecules and molecular complexes. A single molecule may give rise to a variety of polymorphs having distinct crystal structures and physical properties like melting point, thermal behaviors (e.g. measured by thermogravimetric analysis—"TGA", or differential scanning calorimetry—"DSC"), X-ray diffraction pattern, infrared absorption fingerprint, and solid state ($^{13}$C-) NMR spectrum. One or more of these techniques may be used to distinguish different polymorphic forms of a compound.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, changing the dissolution profile in a favorable direction, or improving stability (polymorph as well as chemical stability) and shelf-life. These variations in the properties of different salts and solid state forms may also offer improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities to assess variations in the properties and characteristics of a solid active pharmaceutical ingredient.

Discovering new salts, solid state forms and solvates of a pharmaceutical product may yield materials having desirable processing properties, such as ease of handling, ease of processing, storage stability, and ease of purification or as desirable intermediate crystal forms that facilitate conversion to other polymorphic forms. New solid state forms of a pharmaceutically useful compound can also provide an opportunity to improve the performance characteristics of a pharmaceutical product. It enlarges the repertoire of materials that a formulation scientist has available for formulation optimization, for example by providing a product with different properties, e.g., a different crystal habit, higher crystallinity or polymorphic stability which may offer better processing or handling characteristics, improved dissolution profile, or improved shelf-life (chemical/physical stability). For at least these reasons, there is a need for additional salts and solid state forms (including solvated forms) of trisodium valsartan:sacubitril.

SUMMARY OF THE INVENTION

The present invention provides a solid state form of trisodium valsartan:sacubitril referred hereto as form II and pharmaceutical compositions thereof.

The present invention also encompasses a process for preparing the above solid state form.

The present invention provides a solid state form of trisodium valsartan:sacubitril for use in the preparation of pharmaceutical compositions and/or formulations of this compound.

The present invention also encompasses the use of the solid state form of trisodium valsartan:sacubitril of the present invention for the preparation of pharmaceutical compositions and/or formulations of this compound.

The present invention comprises a process for preparing the above mentioned pharmaceutical compositions. The process comprises combining the trisodium valsartan:sacubitril with at least one pharmaceutically acceptable excipient.

The trisodium valsartan:sacubitril form, and the pharmaceutical compositions and/or formulations of the present invention can be used as medicaments, particularly for the treatment of hypertension and heart failure.

The present invention further provides trisodium valsartan:sacubitril for use in the preparation of other solid state forms of valsartan:sacubitril.

BRIEF DESCRIPTION OF THE DRAWINGS

FIG. 10: Full peak list of trisodium valsartan:sacubitril form II (Table 1).

FIG. 11: Peak list of form II (two theta values) and corresponding d-spacing values as calculated by HighScore software (Table 2).

DETAILED DESCRIPTION OF THE INVENTION

Figure 1:
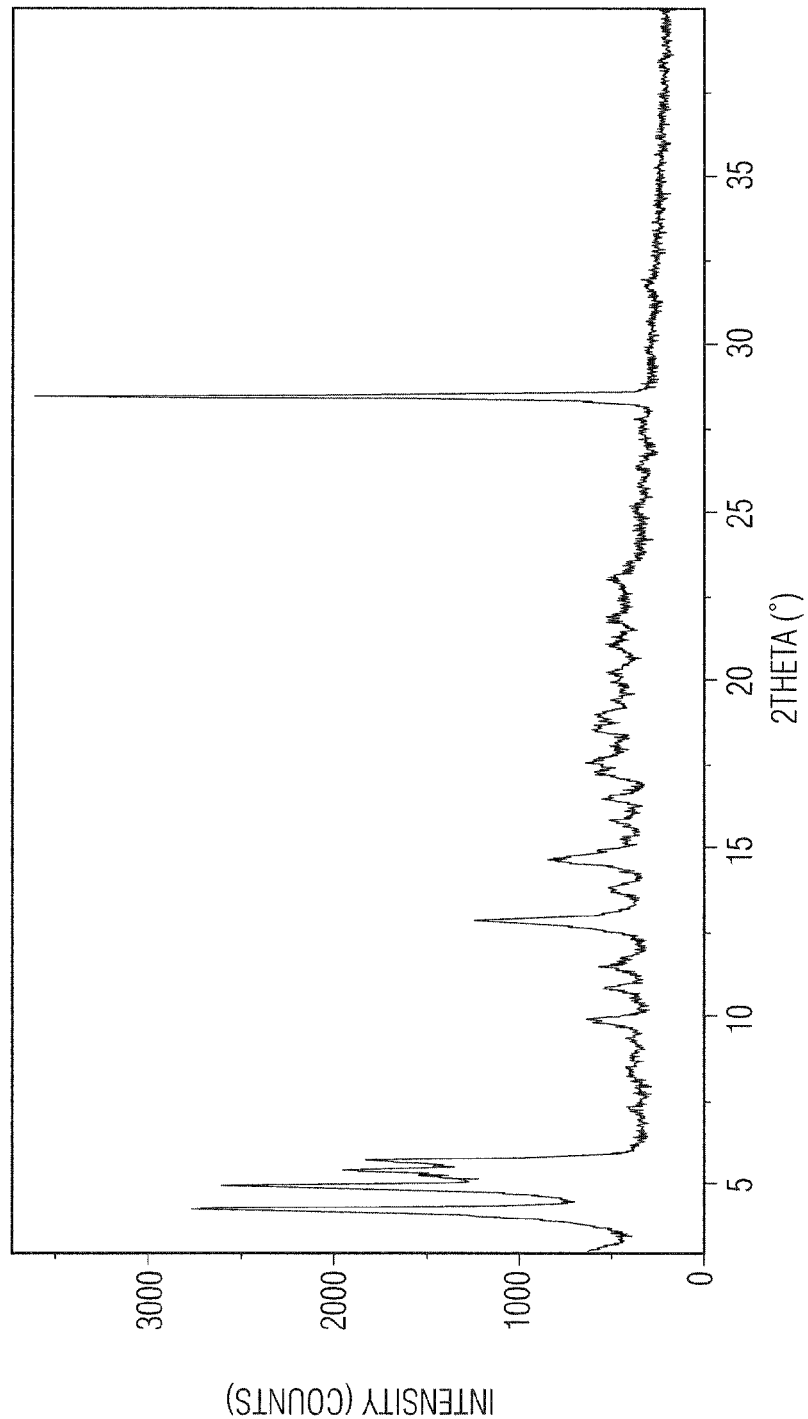
FIG. 1 shows an X-ray powder diffractogram of trisodium valsartan:sacubitril form II.

The present invention encompasses solid state form of trisodium valsartan:sacubitril. Solid state properties of trisodium valsartan:sacubitril can be influenced by controlling the conditions under which the trisodium valsartan:sacubitril is obtained in solid form.

As used herein, valsartan:sacubitril (valsartan:sacubitril cocrystal) also refers to trisodium valsartan:sacubitril cocrystal in hydrate form (also known as LCZ696).

In some embodiments, the solid state form of trisodium valsartan:sacubitril of the invention is substantially free of any other forms of trisodium valsartan:sacubitril.

As used herein, "substantially free" is meant that the solid state form of the present invention contains 20% (w/w) or less of polymorphs, or of a specified polymorph of trisodium valsartan:sacubitril. According to some embodiments, the solid state form of the present invention contains 10% (w/w) or less; or 5% (w/w) or less; or 2% (w/w) or less of polymorphs, or of a specified polymorph of trisodium valsartan:sacubitril. In other embodiments, the solid state form of trisodium valsartan:sacubitril of the present invention contains from 2% to 20% (w/w); or from 5% to 20% (w/w); or from 5% to 10% (w/w) of one or more solid state forms or one or more polymorphs of trisodium valsartan:sacubitril which is/are different from the predominant solid state of trisodium valsartan:sacubitril which is present.

Depending on which other solid state forms comparison is made with, the crystalline form of trisodium valsartan:sacubitril of the present invention has advantageous properties selected from at least one of the following: chemical purity, flowability, solubility, dissolution rate, morphology or crystal habit, stability—such as chemical stability as well as thermal and mechanical stability with respect to polymorphic conversion, stability towards dehydration and/or storage stability, low content of residual solvent, a lower degree of hygroscopicity, flowability, and advantageous processing and handling characteristics such as compressibility, and bulk density. Particularly, the crystalline form of trisodium valsartan:sacubitril of the present invention has good flow and compression properties, which are particularly useful for processing and handling, for example during filtration and formulation processes. In some embodiments, the present invention provides crystalline form of trisodium valsartan:sacubitril having advantageous morphology, in particular uniform morphology.

A solid state form, such as a crystal form or amorphous form, may be referred to herein as being characterized by graphical data "as depicted in" or "as substantially depicted in" a Figure. Such data include, for example, powder X-ray diffractograms and solid state NMR spectra. As is well-known in the art, the graphical data potentially provides additional technical information to further define the respective solid state form (a so-called "fingerprint") which cannot necessarily be described by reference to numerical values or peak positions alone. In any event, the skilled person will understand that such graphical representations of data may be subject to small variations, e.g., in peak relative intensities and peak positions due to certain factors such as, but not limited to, variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of a trisodium valsartan:sacubitril referred to herein as being characterized by graphical data "as depicted in" or "as substantially depicted in" a Figure will thus be understood to include any crystal forms of trisodium valsartan:sacubitril characterized with the graphical data having such small variations, as are well known to the skilled person, in comparison with the Figure.

As used herein, the term "isolated" in reference to solid state form of trisodium valsartan:sacubitril of the present invention corresponds to a solid state form of trisodium valsartan:sacubitril that is physically separated from the reaction mixture in which it is formed.

As used herein, unless stated otherwise, the XRPD measurements are taken using copper Kα radiation wavelength 1.5418 Å.

As used herein, DSC measurements are obtained at a heating rate of 10° C./minute, under a nitrogen flow of 50 ml/min.

As used herein, solid state $^{13}$C NMR was carried out at 125 MHz at 0° C., spinning rate 11 kHz.

As used herein, TGA analysis is carried out at a heating rate of 5° C. per minute to 250° C., preferably with a nitrogen flow of 20 ml/min.

As used herein, circularity refers to the ratio of the perimeter of a circle with the same area as the particle divided by the perimeter of the actual particle image. Circularity is preferably determined by measurement of the particles following sieving through a sieve having a pore size of 300 µm. The particles are preferably measured following analysis of photographs of the particles at an appropriate magnification (e.g. 2.5 to 5.0 times magnification). More particularly, the sample is analyzed using Morphologi G3 instrumentation. The collected data can be processed using image analysis. Circularity is a ratio of the perimeter of a circle with the same area as the particle divided by the perimeter of the actual particle image.

A thing, e.g., a reaction mixture, may be characterized herein as being at, or allowed to come to "room temperature" or "ambient temperature", often abbreviated as "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C.

The amount of solvent employed in a chemical process, e.g., a reaction or a crystallization, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending a 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding solvent X (1.5 v/v) to a 100 ml reaction mixture would indicate that 150 mL of solvent X was added.

A process or step may be referred to herein as being carried out "overnight." This refers to a time interval, e.g., for the process or step, that spans the time during the night, when that process or step may not be actively observed. This time interval is from about 8 to about 20 hours, or about 10-18 hours, typically about 16 hours.

As used herein, the term "reduced pressure" refers to a pressure that is less than atmospheric pressure. For example, reduced pressure is about 10 mbar to about 100 mbar.

As used herein dissipation energy is calculated using Visimix software according to the reactor geometry (e.g. reactor diameter), impeller diameter and impeller type, baffle type and width, clearance of baffle and impeller from bottom of reactor, liquid height and density of the solution or suspension, which can be readily determined by a chemical engineer.

As used herein, and unless indicated otherwise, the terms "wet crystalline form" or "wet form" refer to a polymorph that was not dried using any conventional techniques to remove residual solvent. Examples for such conventional techniques can be, but not limited to, evaporation, vacuum drying, oven drying, drying under nitrogen flow, etc.

As used herein, and unless indicated otherwise, the terms "dry crystalline form" or "dry form" refer to a polymorph that was dried using any conventional techniques to remove residual solvent. Examples for such conventional techniques can be, but not limited to, evaporation, vacuum drying, oven drying, drying under nitrogen flow, etc.

In one embodiment, crystalline form II of trisodium valsartan:sacubitril may be characterized by data selected from one or more of the following: an X-ray powder diffraction pattern having peaks at 5.8, 7.3, 12.9, 15.9, 16.5 and 18.6 degrees two theta±0.2 degrees two theta; and/or an X-ray powder diffraction pattern having peaks at: 7.3, 16.5, 9.4, 10.9 and 14.7 two theta±0.2 degrees two theta; and/or X-ray powder diffraction d-spacings at: 20.341, 15.261, 12.068, 9.397, 8.826, 8.092, 6.863, 6.024, 5.583, 5.353 and 4.773 Å±0.1 Å; and/or a solid state $^{13}$C NMR spectrum having peaks at 176.8, 161.9, 141.1, 139.5, 138.6, 137.2, 129.3, 128.7, 126.3, 124.9, 64.2, 60.6, 47.5, 46.1, 40.1, 39.0, 38.1, 34.3, 32.7, 29.8, 28.2, 22.4, 20.2, 17.8, 16.5, 13.7, 11.7 ppm±0.2 ppm.

Figure 5:
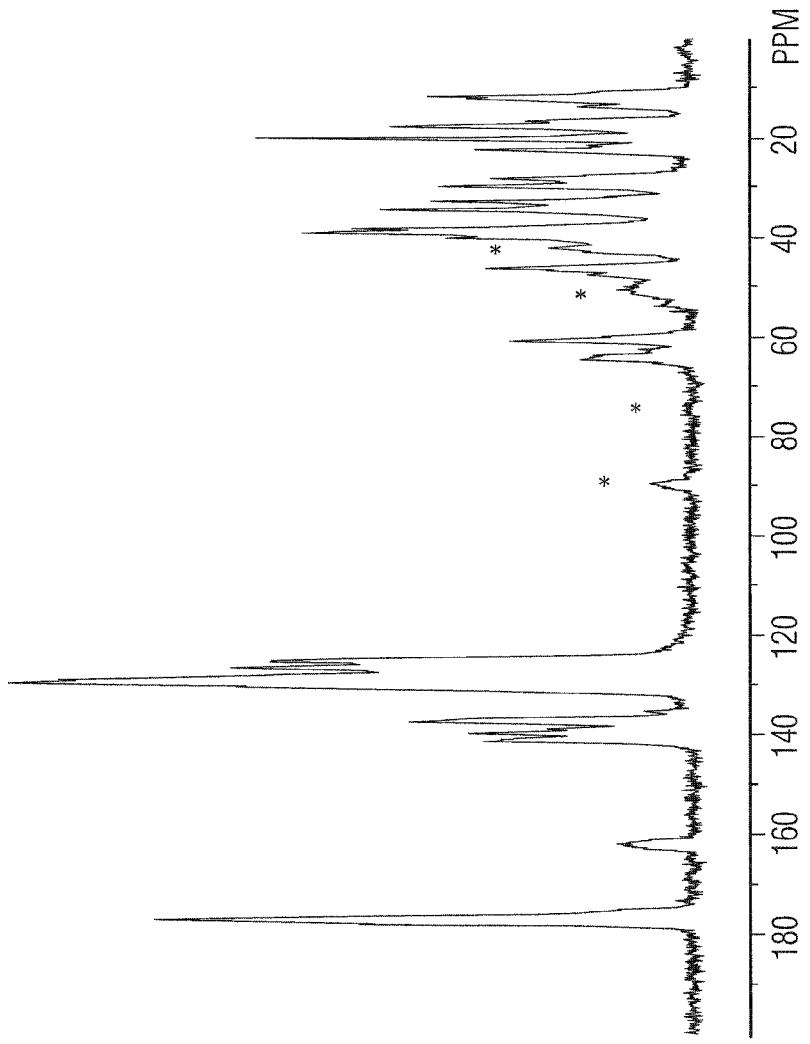
FIG. 5 shows $^{13}$C NMR spectrum of trisodium valsartan:sacubitril form II.

In one embodiment, the present invention comprises crystalline trisodium valsartan:sacubitril, designated form II, characterized by data selected from one or more of the following: X-ray powder diffraction pattern having peaks at 5.8, 7.3, 12.9, 15.9, 16.5 and 18.6 degrees two theta±0.2 degrees two theta; an X-ray powder diffraction pattern as depicted in FIG. 1; a solid-state $^{13}$C NMR spectrum as depicted in FIG. 5; and combinations of this data.

Figure 6:
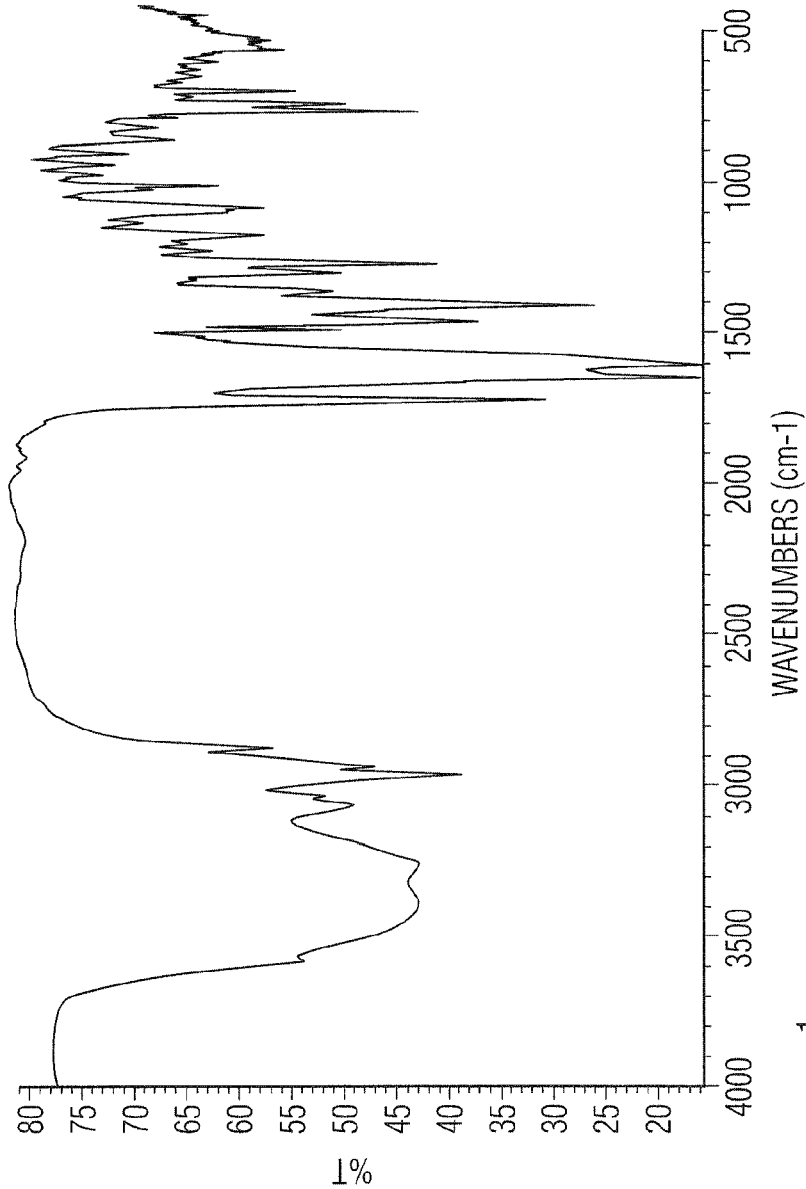
FIG. 6 shows FTIR spectrum of trisodium valsartan:sacubitril form II.

Crystalline form II of trisodium valsartan:sacubitril can be further characterized by: the X-ray powder diffraction pattern having peaks at 5.8, 7.3, 12.9, 15.9, 16.5 and 18.6 degrees two theta±0.2 degrees two theta and also having any one, any two, any three or more additional peaks selected from: 4.3, 9.4, 10.0, 10.9 and 14.7 two theta±0.2 degrees two theta; an FTIR spectrum as depicted in FIG. 6; and combinations of this data.

Figure 14:
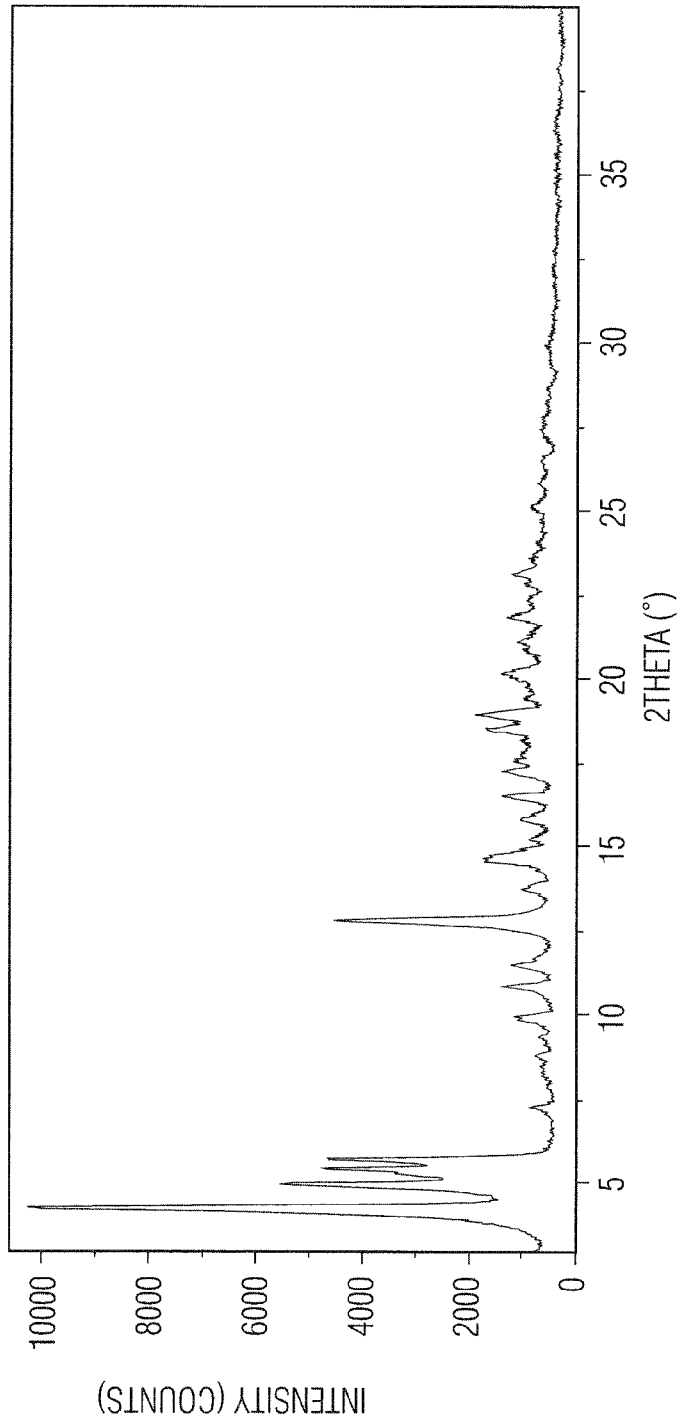
FIG. 14: X-ray powder diffractogram crystalline trisodium valsartan:sacubitril form II prepared according to Example 18.

Alternatively, crystalline form II of trisodium valsartan:sacubitril may be characterized by data selected from one or more of the following: X-ray powder diffraction pattern having peaks at: 7.3, 16.5, 9.4, 10.9 and 14.7 two theta±0.2 degrees two theta; an X-ray powder diffraction pattern as depicted in FIG. 1; a solid-state $^{13}$C NMR spectrum as depicted in FIG. 5; and combinations of this data. In an alternative embodiment, crystalline form II of trisodium valsartan:sacubitril may be characterized by an X-ray powder diffraction pattern substantially as depicted in FIG. 14, and/or a solid-state $^{13}$C NMR spectrum as depicted in FIG. 5.

Crystalline form II of trisodium valsartan:sacubitril can be further characterized by the X-ray powder diffraction pattern having peaks at 7.3, 16.5, 9.4, 10.9 and 14.7 two theta±0.2 degrees two theta and also having any one, any two, any three or more additional peaks selected from: 4.3, 5.8, 10.0, 12.9, 15.9 and 18.6 two theta±0.2 degrees two theta; an FTIR spectrum as depicted in FIG. 6; and combinations of this data.

Crystalline Form II of trisodium valsartan:sacubitril may be characterized by each of the above characteristics alone and/or by all possible combinations.

The full PXRD peak list of crystalline trisodium valsartan:sacubitril form II is specified in Table 1 (peak positions were corrected using silicon standard peak value at 28.45 deg. two theta). A skilled person will be able to identify the peaks that are characteristic for Form II (i.e., not necessarily the most intense peaks) from such a list and, optionally the accompanying PXRD pattern. It is also well known in the art that the intensity of the peaks may exhibit a certain variation; depending on the specific circumstances of the measurement (instruments used, possible orientation effects, etc.). Accordingly, the intensity is often not a useful parameter to unequivocally define a given crystalline form. Typically, a combination of 4-6 peaks that are unique to this specific form are sufficient to define a crystalline form. For example, crystalline form II can be characterized by peaks at 5.8, 7.3, 12.9, 15.9, 16.5 and 18.6 degrees two theta±0.2 degrees two theta, and optionally characterized by any one, any two, any three or more additional peaks selected from: 4.3, 9.4, 10.0, 10.9 and 14.7 two theta±0.2 degrees two theta. It will be appreciated that it may be necessary to use further peaks from the PXRD peak list in order to properly distinguish said crystalline form from other crystalline forms, e.g. crystalline forms that were yet unknown to the inventors at the filing date of this application. It is contemplated that any peak or combination of peaks from said peak list may be used to further define the crystalline form. Accordingly, Form II may optionally be further defined by one, two, three, four, five, or more than five additional peaks from the peak list presented in Table 1. In addition or alternatively, the crystalline Form II may also be further defined by the absence of any peaks (defined as relative intensity I/Io of less than 1%) between any of two neighboring peaks in the peak list. The associated PXRD pattern (see FIG. 1) may assist in identifying such characteristic areas where no peak is present for form II.

Figure 2:
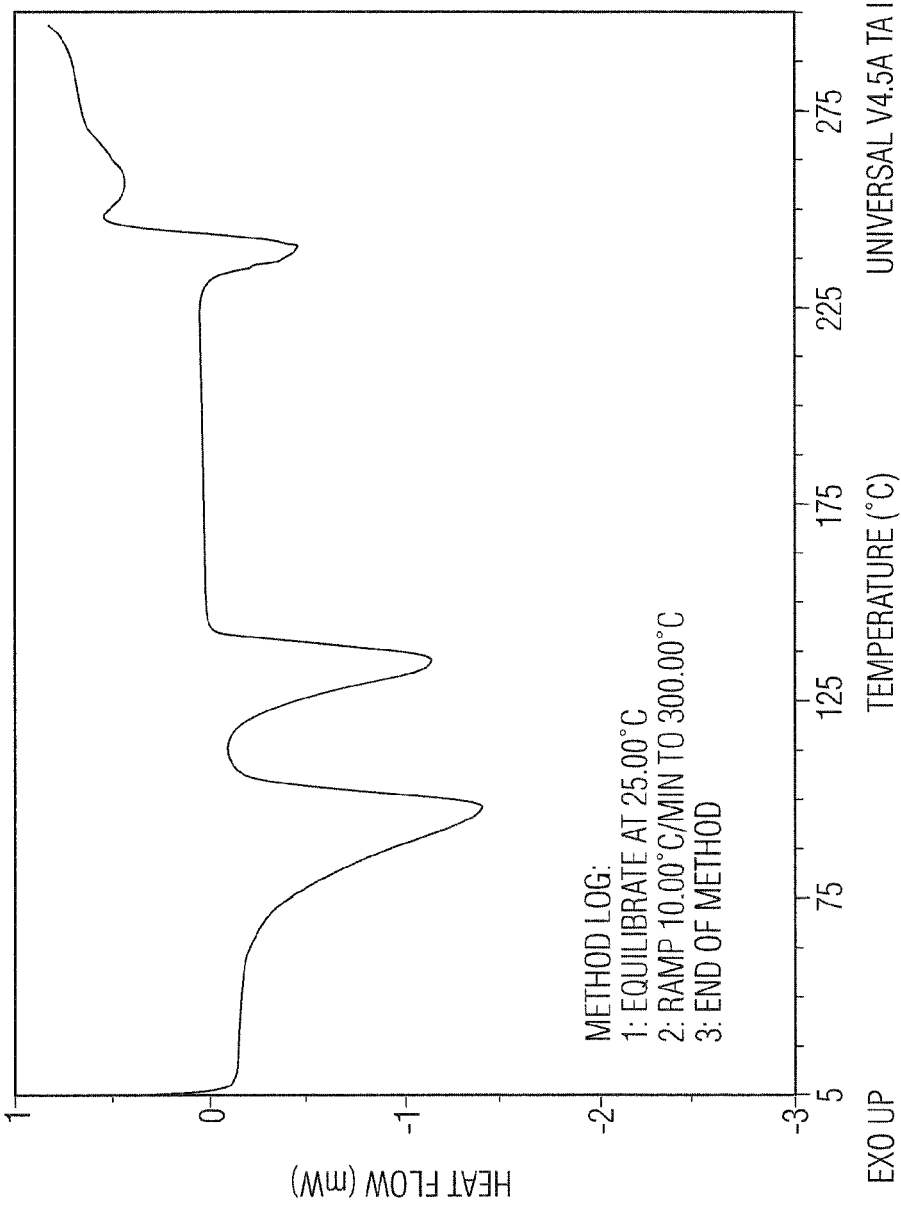
FIG. 2 shows DSC thermogram of trisodium valsartan:sacubitril form II.

Form II of the present invention can be further characterized by differential scanning calorimetry (DSC) as shown in FIG. 2 and/or further characterized by a solid state $^{13}C$ NMR as depicted in FIG. 5.

Form II may in certain embodiments be characterized, alternatively or in addition, by a characteristic d-spacing as shown in Table 2. The d-spacing values are calculated from two-theta values using HighScore software (v. 2.2a), based on Bragg's law. Deviation is 0.1 Å.

In some embodiments, crystalline Form II of the present invention is a hydrate. Preferably the crystalline form may contain from 5.2 to 5.7 wt % water (e.g. as determined by TGA)(i.e., water which is part of the crystal structure).

In some embodiments of the present invention, the crystalline Form II as defined according to any aspect or embodiment described herein, may be provided in a particular morphology. In particular the crystalline Form II may comprise agglomerates having spherical morphology. The agglomerates themselves comprise primary particles. In preferred embodiments, the crystalline Form II comprises: at least 50%, at least 60%, at least 70%, at least 80%, or at least 90% (preferably on a volume basis) of agglomerates having spherical morphology. The degree of spherical morphology can be further defined by circularity. Circularity is the ratio of the perimeter of a circle with the same area as the particle divided by the perimeter of the actual particle image, and can be readily determined by image analysis of the particles. Image analysis may be carried out according to the procedure described below. Preferably, crystalline Form II may comprise agglomerates having spherical morphology such that at least 50% of the particles on a volume basis (v 0.5) is: greater than or equal to about 0.85, about 0.86 to 1, about 0.88 to about 0.98, about 0.90 to about 0.96, about 0.92 to about 0.96. The primary particles forming the aggregates may have a different morphology, for example, plate-like morphology. Crystalline Form II comprising agglomerates having spherical morphology as described herein provides advantageous processing characteristics and/or stability due to particles having uniform morphology.

It has been found that agitation of the mixture during the crystallization of the trisodium valsartan:sacubitril Form II from a solution during a crystallization procedure (for example during, or after—preferably after—a cooling step) can affect the morphology of the product. In particular, it has been found that crystalline Form II comprising agglomerates having spherical morphology as defined herein can be prepared by controlling the agitation (stirring). Particularly, the agitation is conducted at a dissipation energy of ≤2.0 W/kg, more preferably at a dissipation energy of 0.2 to 2.0 W/kg, more preferably at a dissipation energy of 0.5 to 1.5 W/kg, and most preferably at a dissipation energy of 0.5 to 1 W/kg. The agitation can be carried out for: about 0.1 to about 5 hours, about 0.25 to about 4 hours, or about 1 to about 3 hours. Preferably, the dissipation energy is set to 1.7 or lower after crystallization occurs. Preferably the agitation is carried out at a temperature of 45-55° C.

Crystalline Form II of the present invention and pharmaceutical compositions containing crystalline Form II can be prepared according to the processes described herein. Preferably, the processes as described herein are carried out such that the crystallization of the Form II is done in the presence of water, for example either water added during the reaction or residual water in the solvents or reactants or water present in the starting materials (e.g. such as LCZ696 which is a hydrated form, valsartan disodium hydrate—e.g. valsartan disodium trihydrate) or in the presence of atmospheric water, or by a step of exposure to high relative humidity.

A process for preparing a crystalline form II of trisodium valsartan:sacubitril comprising: (i) combining trisodium valsartan:sacubitril (preferably in hydrate form, e.g. LCZ696) with a solvent and heating (preferably to a temperature of about 80° C. to about 150° C., about 90° C. to about 130° C.) to form a solution, preferably wherein the solvent comprises an aromatic solvent, preferably toluene and/or methyl benzoate; (ii) cooling the solution (preferably to a temperature of about 4-28° C., preferably about 5 to about 25° C. and more preferably about 5 to about 20° C.) to obtain a mixture, and (iii) isolating the crystalline form from the mixture, preferably wherein the trisodium valsartan sacubitril is a hydrate form. Alternatively crystalline form II of trisodium valsartan:sacubitril comprising can be prepared by a process comprising: (i) combining disodium valsartan (preferably in hydrate form, and more preferably a trihydrate) and sacubitril sodium with a solvent (preferably wherein the solvent is or comprises toluene) to form a solution, (ii) cooling and/or removing at least a portion of the solvent to obtain a mixture, and (iii) isolating the crystalline form from the mixture. In these processes, step (iii) can comprise filtering the mixture from step (ii), and exposing the resulting solid to a relative humidity of about 40 to 80%, preferably 50 to 70% and more preferably about 60%. Alternatively, in the process combining disodium valsartan (preferably in hydrate form, and more preferably a trihydrate) and sacubitril sodium the isolating step can comprise filtering the mixture obtained in step (ii), slurrying the solid in a solvent comprising a C6-C10 alkane, preferably n-heptane, and isolating the crystalline form.

In another aspect of the present invention, there is provided a process for preparing a crystalline form II of trisodium valsartan:sacubitril comprising: (i) providing a solution of sacubitril in a solvent, preferably wherein the solvent is water immiscible, more preferably wherein the solvent comprises ethyl acetate and/or toluene, and most preferably wherein the solvent is ethyl acetate or toluene, (ii) adding valsartan acid and a sodium base, preferably sodium carbonate or sodium hydroxide, and more preferably in a molar equivalent of about 2.8 to about 3.2 moles of sodium per mole of valsartan or sacubitril, to the sacubitril solution, and (iii) isolating the crystalline form. Optionally, after adding the valsartan acid and sodium base and prior to isolating the crystalline form, the following steps can be carried out (ii-a) optionally removing the solvent, (ii-b) optionally adding toluene and water to form a mixture, (ii-c) optionally heating the mixture, and (ii-d) cooling the mixture. Preferably, the process comprises the steps of: (i) providing a solution of sacubitril in a solvent (preferably wherein the solvent is water immiscible and more preferably wherein the solvent comprises ethyl acetate and/or toluene, and most preferably wherein the solvent is ethyl acetate or toluene), (ii) adding valsartan acid and a sodium base (preferably sodium carbonate or sodium hydroxide, and more preferably in a molar equivalent of about 2.8 to about 3.2 moles of sodium per mole of valsartan or sacubitril), to the sacubitril solution, (ii-a) optionally removing the solvent, (ii-b) optionally adding toluene and water to form a mixture, (ii-c) optionally heating the mixture, (vii-d cooling the mixture, and (iii) isolating the crystalline form from the mixture. Step (iii) can comprise filtering the mixture from step (ii-b) or (ii-d), suspending the resulting solid in a solvent (preferably wherein the solvent is or comprises a C6-C10 alkane, more preferably heptane), and filtering. In a preferred embodiment, the solution of sacubitril in a solvent is prepared by combining an alkali or alkali earth metal salt of sacubitril, preferably in the form of a hydrate, in the solvent (preferably wherein the solvent comprises ethyl acetate or toluene), and acidifying with an aqueous mineral acid, preferably hydrochloric acid, and removing the aqueous layer. Preferably sacubitril hemicalcium salt is used, and the crystallization of form II is conducted in the presence of water. The use of water in an amount of about 94 to about 138 ml of water (more preferably about 120 to about 130 ml of water) water per kg of sacubitril hemicalcium salt is preferred. The amount of water is calculated with respect to sacubitril hemicalcium in anhydrous form. The preferred amount of water present is preferably calculated depending on the assayed amount of water present in the reaction. Thus, preferably, the amount of water already present in the reaction is determined, and is subtracted from the amount of 94 to about 138 ml (per kg of sacubitril hemicalcium), and only the difference to make the quantity up to about 94 to about 138 ml (or 120 to 130 ml) per kg of sacubitril hemicalcium salt is added.

In another aspect, the present invention provides a process for preparing a crystalline form II of trisodium valsartan:sacubitril comprising: (i) combining valsartan acid and sacubitril acid with an organic solvent, preferably wherein the solvent comprises ethyl acetate, (ii) adding aqueous sodium hydroxide, preferably in a molar equivalent amount of 3.0-3.1 per mole of valsartan add or relative to sacubitril acid, to form a mixture, and (iii) isolating the crystalline form. Preferably, after adding the aqueous sodium hydroxide, and prior to isolating the crystalline form, the following steps are carried out: (ii-a) optionally removing a portion of the solvent, (ii-b) adding an organic solvent, preferably comprising toluene to the mixture, (ii-c) optionally concentrating the mixture, (ii-d) optionally repeating step (ii-b), (ii-e) heating the mixture, (iii-f) cooling the mixture, and (ii-g) filtering the resulting solid and subjecting the solid to a relative humidity of about 40 to 80%, preferably 50 to 70% and more preferably about 60%. In a preferred embodiment, the process comprises the steps of (i) combining valsartan acid and sacubitril acid with an organic solvent, preferably wherein the solvent comprises ethyl acetate; (ii) adding aqueous sodium hydroxide, preferably in a molar equivalent amount of 3.0-3.1 per mole of valsartan acid or relative to sacubitril acid, to form a mixture; (ii-a) optionally removing a portion of the solvent; (ii-b) adding an organic solvent, preferably comprising toluene to the mixture; (ii-c) optionally concentrating the mixture; (ii-d) optionally repeating step (ii-b); (ii-e) heating the mixture; (ii-f) cooling the mixture; (ii-g) filtering the resulting solid and subjecting the solid to a relative humidity of about 40 to 80%, preferably 50 to 70% and more preferably about 60%; and (iii) isolating the crystalline form from the mixture.

The crystallization processes of the present invention can advantageously be used to prepare crystalline form II of trisodium valsartan:sacubitril comprising aggregates having spherical morphology as described in any embodiment of the present invention disclosed herein. The applicant has found that the morphology of the aggregates can be controlled by agitating (stirring) the mixture during and/or after (preferably after) cooling provided that the agitation is conducted at a dissipation energy of ≤2.0 W/kg. Preferably, the agitation or stirring is carried out at a dissipation energy of 0.2 to 2.0 W/kg, more preferably at a dissipation energy of 0.5 to 1.5 W/kg, and most preferably at a dissipation energy of 0.5 to 1 W/kg. Preferably the agitation is carried out for a sufficient time to enable to production of aggregates having spherical morphology. For example, the mixture can be agitated for: about 0.1 to about 5 hours, about 0.25 to about 4 hours, or about 1 to about 3 hours.

In accordance with another aspect of the present invention, there is provided a process for preparing a crystalline form II of trisodium valsartan:sacubitril comprising homogenizing (e.g. grinding in a mortar) a mixture of valsartan acid, sacubitril sodium and sodium hydroxide, preferably in a molar equivalent amount of 2.0-2.1 per mole of valsartan acid, in a solvent to form a mixture, preferably wherein the solvent comprises toluene. The homogenizing is preferably conducted in air, i.e. in the presence of atmospheric water.

Another aspect of the invention provides a process for preparing a crystalline form II of trisodium valsartan:sacubitril comprising suspending a mixture of valsartan disodium (preferably in hydrated form) and sacubitril sodium in a solvent (preferably wherein the solvent is, or comprises, toluene and/or 2-methyl tetrahydrofuran). The suspending may be carried out for a sufficient time to form crystalline Form II, for example, the suspending may be carried out for about 0.5 to about 12 hours, more preferably for about 1 to about 8 hours, and particularly for about 2 to about 5 hours.

Also provided in another aspect of the present invention, is a process for preparing crystalline form II of trisodium valsartan:sacubitril comprising contacting trisodium valsartan:sacubitril, preferably in amorphous form with a solvent comprising at least one of t-butyl methyl ether, 2-methyl tetrahydrofuran, or an aromatic solvent, preferably toluene or methyl benzoate, wherein the contacting is preferably carried out at room temperature. In a preferred embodiment, the contacting comprises exposing the amorphous trisodium valsartan:sacubitril to vapours of the solvent, preferably for about 2 to about 14 days, more preferably for about 3-10 days, and particularly for about 5-8 days. Alternatively, the contacting comprises slurrying amorphous trisodium valsartan:sacubitril in the solvent, for a sufficient time to form crystalline Form II. Preferably the slurrying is carried out for about 0.5 to about 12 hours, more preferably for about 2 to about 8 hours, and particularly for about 2 to about 6 hours, and optionally isolating the crystalline form.

In a further aspect of the present invention, there is provided a process for preparing crystalline trisodium valsartan:sacubitril form II in a solvent comprising combining trisodium valsartan:sacubitril (preferably in hydrated form, such as LCZ696) with an aromatic solvent (preferably wherein the aromatic solvent is selected from chlorobenzene, fluorobenzene, m-xylene, o-xylene, p-xylene, anisole and methyl benzoate, and most preferably methyl benzoate), heating the mixture to form a solution, cooling the solution, and optionally isolating the form II. Prior to isolating the form II, the cooled solution is allowed to evaporate.

The above crystalline Form II of trisodium valsartan:sacubitril may be obtained either as a wet form, or a dry form.

In any of the aforementioned processes, the form II may be isolated and dried. The drying can optionally be carried out under reduced pressure, and optionally with heating, or the form II may be allowed.

The present invention further comprises a process as defined above, which further comprises combining the crystalline form of trisodium valsartan:sacubitril with at least one pharmaceutically acceptable excipient to form a pharmaceutical composition.

The present invention further encompasses a crystalline form of trisodium valsartan:sacubitril obtainable or obtained by any process as defined in any embodiment or aspect described herein.

Crystalline form II trisodium valsartan:sacubitril according to any aspect of the present invention or crystalline form II trisodium valsartan obtainable or obtained by the processes as described in any aspect or embodiment disclosed herein may be combined with at least one pharmaceutically acceptable excipient to form a pharmaceutical composition.

The invention further comprises crystalline trisodium valsartan:sacubitril according to present invention or prepared by the processes described herein for use as a medicament, preferably for the treatment of hypertension and heart failure.

The above described solid state form can be used to prepare 1) other solid state forms of trisodium valsartan:sacubitril; or 2) solid state forms of valsartan:sacubitril; or 3) other salts of valsartan:sacubitril and their solid state forms. The present invention encompasses a process for preparing other salts of valsartan:sacubitril or solid state forms thereof. The process comprises preparing form II of trisodium valsartan:sacubitril by the processes of the present invention, and converting it to said other valsartan:sacubitril salt. The conversion can be done, for example, by a process comprising acidifying the above described form II of trisodium valsartan:sacubitril, and reacting the obtained valsartan:sacubitril acid with an appropriate base, to obtain the corresponding salt. Alternatively, the conversion can be done by salt switching, i.e., reacting the trisodium valsartan:sacubitril, with a base having a $pK_a$ which is higher than the $pK_a$ of the base of trisodium valsartan:sacubitril salt.

The above described solid state form of trisodium valsartan:sacubitril can be used to prepare chemically pure valsartan:sacubitril or salts thereof. In certain embodiments, the present invention encompasses the above described solid state form of trisodium valsartan:sacubitril for use in the chemical purification of valsartan:sacubitril, and salts thereof.

The present invention further encompasses a process for chemical purification of trisodium valsartan:sacubitril. The process comprises crystallizing form II of trisodium valsartan, preferably by the process of the present invention. In certain embodiments, the present invention comprises a process for chemical purification of trisodium valsartan:sacubitril comprising crystallizing trisodium valsartan:sacubitril from toluene.

The above described solid state forms of trisodium valsartan: sacubitril can be used to prepare pharmaceutical compositions and formulations. In certain embodiments, the present invention comprises the above described solid state forms of trisodium valsartan: sacubitril for use in the preparation of pharmaceutical compositions and formulations.

The present invention comprises pharmaceutical compositions and formulations comprising trisodium of valsartan:sacubitril of the present invention. Typically, the pharmaceutical composition is a solid composition and the trisodium valsartan:sacubitril retains its solid state form.

The pharmaceutical compositions can be prepared by a process comprising combining the solid state form of trisodium valsartan:sacubitril of the present invention with at least one pharmaceutically acceptable excipient.

The above solid state form of trisodium valsartan:sacubitril and/or pharmaceutical compositions of the present invention can also be used as a medicament.

The present invention further encompasses 1) the use of the above-described solid state form of trisodium valsartan:sacubitril in the manufacture of a pharmaceutical composition, and 2) a method of treating a subject suffering from hypertension, or otherwise in need of the treatment, comprising administration of an effective amount of a pharmaceutical composition comprising the above crystalline form of trisodium valsartan:sacubitril described herein to a person in need of the treatment.

The present invention further provides a method of treating a subject suffering from hypertension or heart failure, comprising administration of an effective amount of a pharmaceutical composition comprising a crystalline form II of trisodium valsartan:sacubitril as defined in any aspect or embodiment disclosure herein, to a subject in need thereof.

Figure 12:
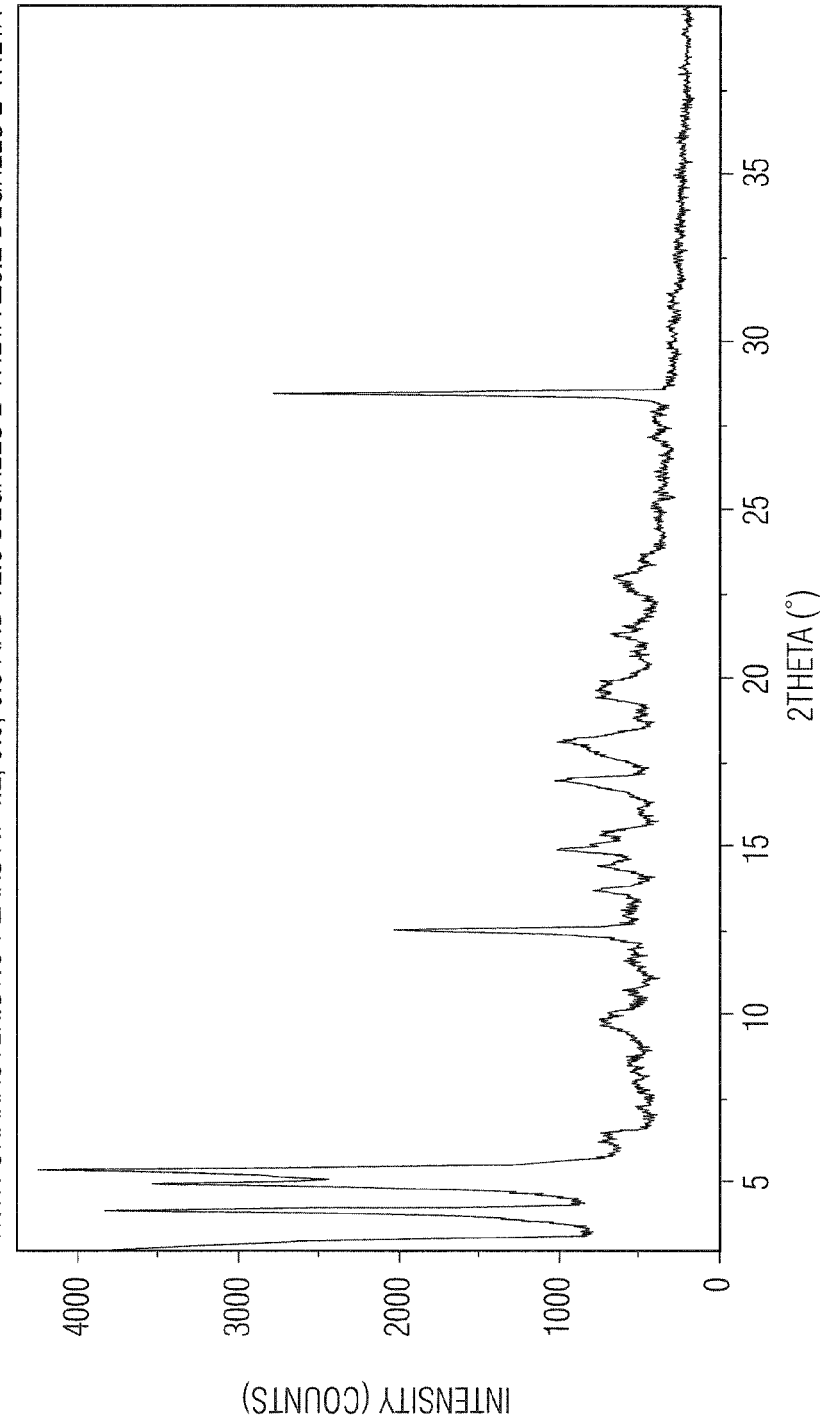
FIG. 12 shows an X-ray powder diffractogram of LCZ696 with characteristic peaks at 4.2, 5.0, 6.5 and 12.6 degrees 2-theta±0.2 degrees 2-theta.

Another aspect of the present invention provides a process for preparing a crystalline form of trisodium valsartan:sacubitril (preferably in hydrated form), wherein the crystalline form is characterized by data selected from: (i) an X-ray powder diffraction pattern having peaks at 4.2, 5.0, 6.5 and 12.6 degrees two theta±0.2 degrees two theta; and optionally, one, two three or four additional peaks at 6.2 13.7, 14.9 and 15.4 degrees two theta±0.2 degrees two theta; or (ii) an X-ray powder diffraction pattern having peaks at 4.2, 5.0, 6.5 and 12.6 degrees two theta±0.2 degrees two theta; and additional peaks at 6.2 13.7, 14.9 and 15.4 degrees two theta±0.2 degrees two theta; or (iii) an X-ray powder diffraction pattern substantially as depicted in FIG. 12, wherein the process comprises crystallising trisodium valsartan:sacubitril (preferably in hydrated form) from a solvent comprising acetonitrile, acetone, ethyl acetate or isopropyl acetate, or a combination thereof. Preferably, the process comprises: suspending valsartan disodium trihydrate and sacubitril sodium in a solvent comprising acetonitrile, acetone, ethyl acetate or isopropyl acetate, optionally with stirring, and (b) optionally isolating the crystalline form. The solvent in step (a) is preferably acetonitrile. Step (a) is preferably carried out for a period of from about 1 to about 18 hours, preferably from about 1 to about 12 hours, more preferably from about 2 to about 10 hours. Preferably, step (a) is carried out at a temperature of about 15 to about 40° C., preferably about 20 to about 30° C. Preferably, step (b) comprises filtering the solid and optionally drying the product, wherein the drying is preferably conducted at a temperature of about 15 to about 40° C., preferably about 20 to about 30° C. In a further embodiment, the present invention encompasses a crystalline form obtainable or obtained by this process. The invention further encompasses a pharmaceutical composition comprising a crystalline form obtainable by this process. In another embodiment, the process further comprises combining the crystalline form with at least one pharmaceutically acceptable excipient to form a pharmaceutical composition.

Having thus described the invention with reference to particular preferred embodiments and illustrative examples, those in the art can appreciate modifications to the invention as described and illustrated that do not depart from the spirit and scope of the invention as disclosed in the specification. The Examples are set forth to aid in understanding the invention but are not intended to, and should not be construed to limit its scope in any way.

X-Ray Powder Diffraction Method:

After the sample was powdered in a mortar and pestle it was applied directly on a silicon plate holder. The X-ray powder diffraction pattern was measured with Philips X'Pert PRO X-ray powder diffractometer, equipped with Cu irradiation source=1.54184 Å (Ångström), X'Celerator (2.022° 2θ) detector. Scanning parameters: angle range: 3-40 deg., step size 0.0167, time per step 37 s, continuous scan. The described peak positions were determined using silicon powder as an internal standard in an admixture with the sample measured. Due to number rounding the position of a few peaks was corrected based on the Si position.

DSC Method:

DSC analysis was performed on Q1000 MDSC (TA instruments) with heating rate of 10° C./min, under nitrogen flow of 50 ml/min. A hermetic aluminium, closed pan with hole was used, and the sample mass was about 1-5 mg.

$^{13}$C NMR Method:

Solid-state $^{13}$C NMR spectra were recorded with variable amplitude cross polarization, magic angle spinning and high power proton decoupling using a BRUKER Avance II+ spectrometer operating at 125 MHz and controlled temperature (0° C.). A probe using 4 mm o.d. zirconia rotors was employed. The operation conditions were: contact time: 2 ms; recycle delay: 4 s; 1024 scans and spin rate of 11 kHz. Chemical shifts were referenced via a replacement sample of glycine (carboxyl carbon chemical shift assigned as 176.03 ppm relative to the signal of tetramethylsilane).

FTIR Method:

1-2 mg of sample was triturated with 200-300 mg of dry potassium bromide and mixture was compressed into a pellet with pressure of 700 MPa. The spectrum of the sample was recorded over the range from 4000 to 400 cm$^{-1}$, with resolution 2 cm$^{-1}$ and 16 scans. For background spectrum air was used (empty sample compartment). Analysis was done on Nicolet 6700.

SEM Method:

SEM micrographs were taken on Joel JSM-5800 scanning microscope at 20 kV, WD 20-22, low current. Samples were sputtered with gold by Edwards S150 sputter coater.

Circularity Method:

Sample was sieved through a sieve with pore size 300 µm. The sieved material was dispersed on the glass surface at 0.5 bar and then images were taken at 2.5-5.0× magnification using Morphologi G3 (Malvern). Collected data was processed using image analysis. Circularity is a ratio of the perimeter of a circle with the same area as the particle divided by the perimeter of the actual particle image.

TGA Method:

Thermogravimetric analysis was carried out on Mettler Toledo TG-DSC 1 with the following method: 5 mg of sample was placed in closed aluminum pan with the pin hole. The sample was heated at a heating rate of 5° C. per minute to 250° C., and purging with nitrogen with flow 20 ml/min.

EXAMPLES

Reference Example

The starting trisodium valsartan: sacubitril can be prepared according to the examples of U.S. Pat. No. 8,877,938.

Example 1: Preparation of Crystalline Trisodium Valsartan:Sacubitril Form II 1.0 g of trisodium valsartan:sacubitril was suspended in toluene (20 ml) and heated to 105-110° C. (clear solution was formed). The clear solution was stirred for 10 minutes at reflux temperature and was cooled down to 20° C., stirred for 1 hour, cooled down to 5° C. and stirred for 1 hour. The mixture was filtered off and the product was left at 20° C. for 20 hours. The crude material was further dried at 50° C. for 20 hours under vacuum. The dried solid material was analyzed by XRPD-form II was obtained. The XRPD pattern of the obtained form is shown in FIG. 1. FIG. 2 shows the DSC of the obtained product.

Example 2: Preparation of Crystalline Trisodium Valsartan:Sacubitril Form II 30 mg trisodium Valsartan:sacubitril cocrystal was suspended in toluene (10 ml) and heated at 105-110° C. to obtain a clear solution. The clear solution was cooled down to room temperature and left to evaporate for 24 hours. The obtained product was analyzed by XRD and DSC-form II.

Figure 3:
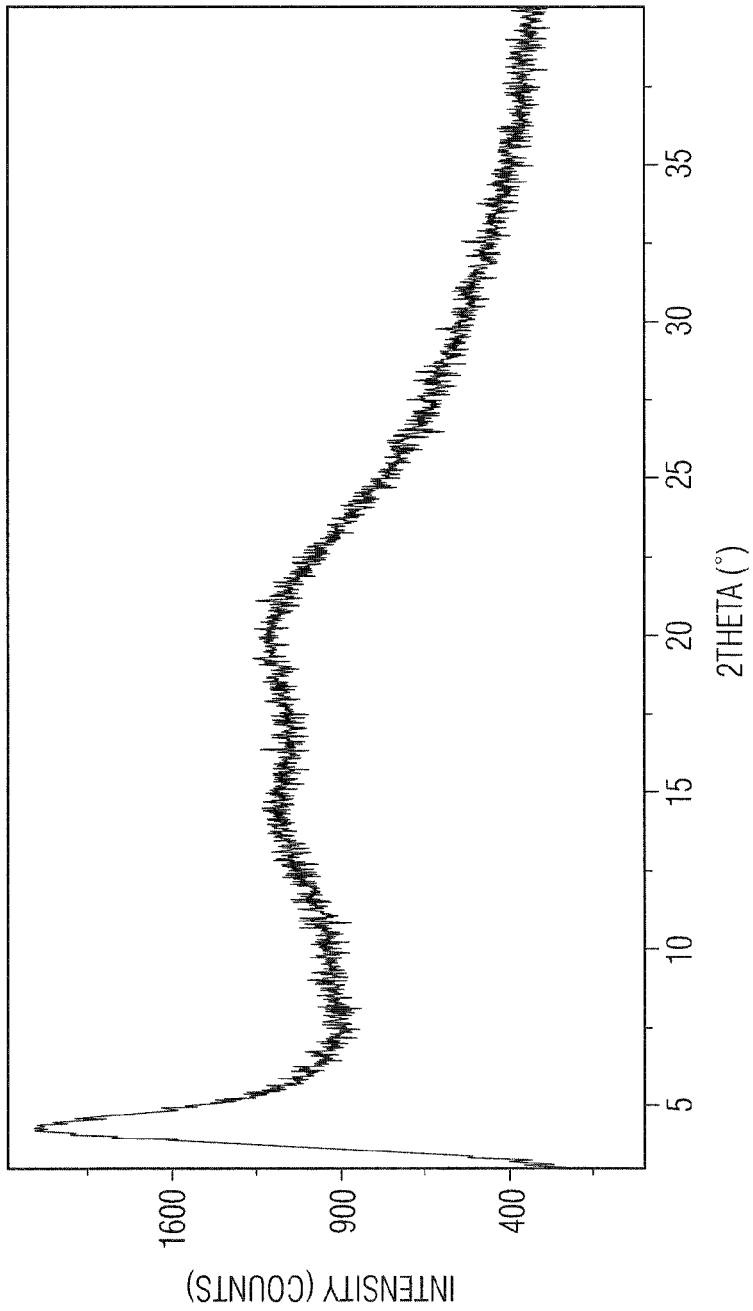
FIG. 3 shows an X-ray powder diffractogram of amorphous trisodium valsartan:sacubitril.
Figure 4:
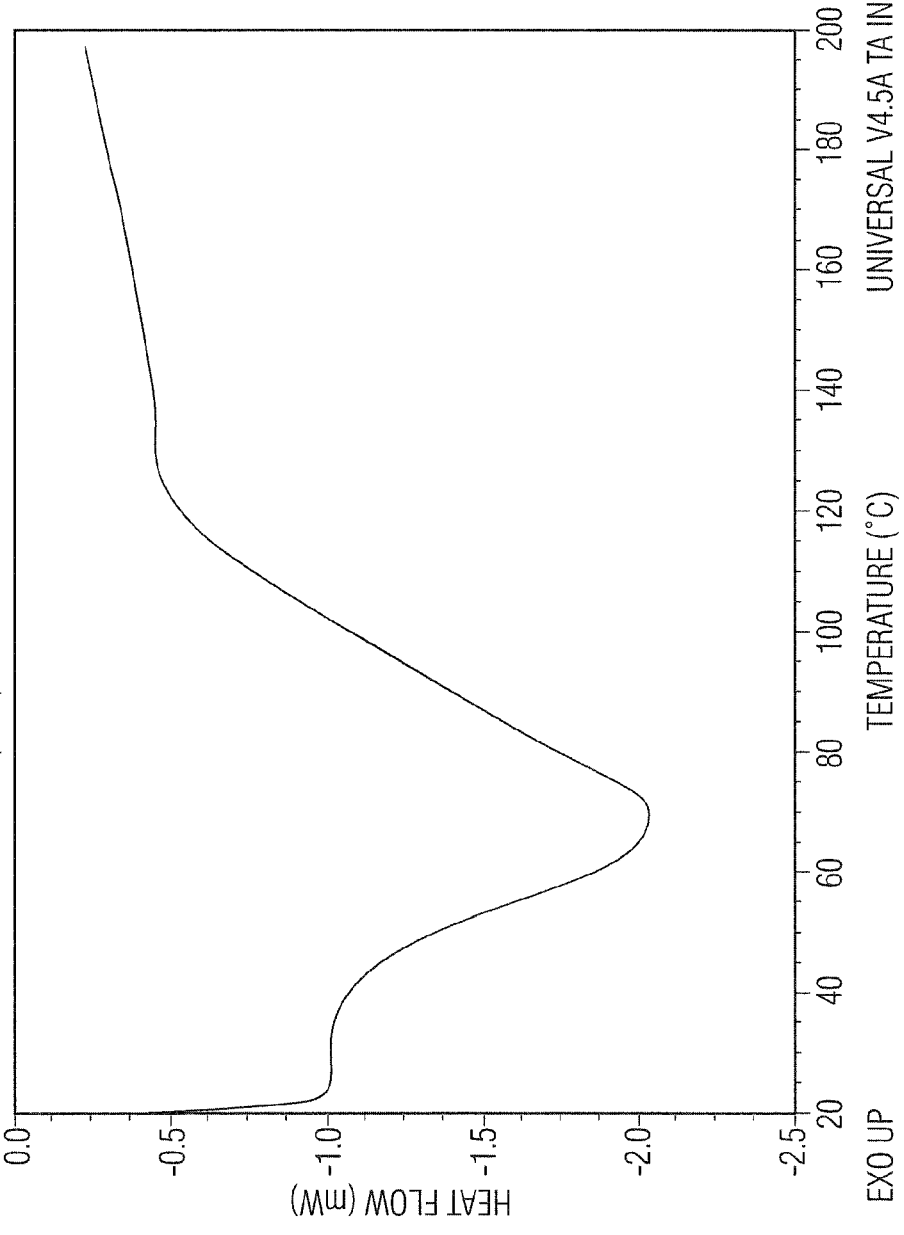
FIG. 4 shows DSC thermogram of amorphous trisodium valsartan:sacubitril.

Example 3: Preparation of Amorphous Trisodium Valsartan:Sacubitril 5 g of trisodium valsartan:sacubitril cocrystal was dissolved in ethanol at 20° C. The solution was then spray dried at the following conditions: Pump 20%, Aspirator 100%, TinI 100° C., Tout 50° C. The obtained white powder was analyzed by XRPD-amorphous. The XRPD pattern of the obtained material is shown in FIG. 3.

Example 4: Preparation of Crystalline Trisodium Valsartan:Sacubitril Form II

Valsartan acid (103 mg) and Sacubitril sodium (102 mg) were homogenized in mortar then 2 ml of toluene and 21 mg of crude sodium hydroxide were added, reaction mixture was stirred for 5 minutes. Crude product was analyzed by XRPD and DSC-form II.

Example 5: Preparation of Crystalline Trisodium Valsartan:Sacubitril Form II 5.0 g of trisodium Valsartan-Sacubitril cocrystal (LCZ696) was suspended in 20 ml of toluene and 0.04 ml of water. The mixture was heated to 110° C. and cooled down to room temperature. Reaction mixture was filtrated off and wet sample was left at 60% RH at 20° C. for 20 hours. Sample was dried 8 h at 40° C. and analyzed by XRPD and DSc-form II.

Example 6: Preparation of Crystalline Trisodium Valsartan:Sacubitril Form II 5.0 g of trisodium Valsartan-Sacubitril cocrystal (LCZ696) was suspended in 20 ml of toluene and 0.1 ml of water. The mixture was heated at 110° C. and cooled down to room temperature. Reaction mixture was filtrated off and wet sample was left at 60% RH at 20° C. for 20 hours. Sample was dried 8 h at 40° C. and analyzed by XRPD and DSC-form II.

Example 7: Preparation of Crystalline Trisodium Valsartan:Sacubitril Form II

Valsartan di Sodium trihydrate (1.05 g) and Sacubitril Sodium (0.950 g) were dissolved in toluene (30 ml) by heating to 110° C. Reaction mixture was stirred for 10 minutes at 110° C. and then cooled down. Reaction mixture was filtrated off, and wet sample was left at 60% RH for 20 hours and then dried at 40° C. under reduced pressure for 8 hours. Product was analyzed by XRPD-solid form II.

Example 8: Preparation of Crystalline Trisodium Valsartan:Sacubitril Form II

Valsartan acid (1.0 g) and Sacubitril add (0.940 g) were dissolved in ethyl acetate and stirred for 15 minutes. Sodium hydroxide (25% aqueous solution, 1.08 ml) and the obtained suspension was stirred for 2 hours. Reaction mixture was concentrated under reduced pressure at 40° C., and then toluene (15 ml) was added. Reaction mixture was once again concentrated under reduced pressure and 40° C. followed again by the addition of toluene (15 ml). Reaction mixture was heated to 110° C., stirred for 10 minutes, cooled down and filtrated off. The wet sample was left at 60% RH for 96 hours and then dried at 40° C. under reduced pressure for 8 hours and analyzed by XRPD-form II.

Example 9: Preparation of Crystalline Trisodium Valsartan:Sacubitril Form II trisodium Valsartan:Sacubitril (LCZ696, 5 g) was suspended in toluene (20 ml) and heated to 105-110° C. Solution was stirred for 5 minutes at reflux temperature and cooled down to 20° C. Wet sample was dried at 50° C. for 24 hours under vacuum. White powder was obtained and analyzed by XRD-form II.

Example 10: Preparation of Crystalline Trisodium Valsartan:Sacubitril Form II

Amorphous trisodium salt of valsartan:sacubitril (100 mg) was exposed to atmosphere vapors of t-butyl methyl ether for 7 days at room temperature. The obtained product was analyzed by XRPD-form II.

Example 11: Preparation of Crystalline Trisodium Valsartan:Sacubitril Form II

Amorphous trisodium salt of valsartan:sacubitril (100 mg) was exposed to atmosphere vapor of toluene for 7 days at room temperature. The obtained product was analyzed by XRPD-form II.

Example 12: Preparation of Crystalline Trisodium Valsartan:Sacubitril Form II

Amorphous trisodium salt of valsartan:sacubitril (500 mg) was suspended in toluene (0.5 ml) and stirred for 4 hours. The obtained product was analyzed by XRPD-form II.

Example 13: Preparation of Crystalline Trisodium Valsartan:Sacubitril Form II

Amorphous trisodium salt of valsartan:sacubitril (500 mg) was suspended of t-butyl methyl ether (0.5 ml) and stirred for 4 hours. The obtained product was analyzed by XRPD-form II.

Example 14: Preparation of Crystalline Trisodium Valsartan:Sacubitril Form II

Valsartan disodium trihydrate (100 mg) and sacubitril sodium (100 mg) were suspended in toluene (2 ml) for 3 hours. The obtained product was analyzed by XRPD-form II.

Example 15: Preparation of Crystalline Trisodium Valsartan:Sacubitril Form II

Valsartan disodium trihydrate (100 mg) and sacubitril sodium (100 mg) were suspended in 2-methyl-tetrahydrofuran (2 ml) for 3 hours. The obtained product was analyzed by XRPD-form II.

Example 16: Preparation of Amorphous Trisodium Valsartan:Sacubitril

Equivalent amounts of valsartan disodium trihydrate and sacubitril sodium in total mass of mixture (5.0 g) were dissolved in ethanol (96%, 75 ml). Solution was spray dried with inlet temperature 100° C., pump rate 20% and aspiration rate 75%. Powder obtained by spray drying was characterized by XRPD and was found to be amorphous.

Example 17: Preparation of Amorphous Trisodium Valsartan:Sacubitril

Valsartan disodium trihydrate (8.0 g) and sacubitril sodium (7.24 g) were dissolved in toluene (230 ml) at reflux temperature. The solution was then cooled down from reflux to 20° C. with a cooling rate of 15° C./h. Precipitation occurred at 36° C. Upon reaching 20° C., toluene was decanted off and the wet product was suspended in n-heptane (616 ml) and agitated at 20-25° C. for 30 min. The suspension was filtered over a Büchner funnel under nitrogen and the wet product was dried at 40° C. under reduced pressure until constant mass was obtained. The obtained product was analyzed by XRPD-Amorphous.

Example 18: Preparation of Crystalline Trisodium Valsartan:Sacubitril Form II

In a 3 l jacketed glass reactor, valsartan disodium trihydrate (70.4 g) and sacubitril sodium (57.2 g) were dissolved in toluene (2410 ml) at reflux temperature. The solution was cooled down from reflux to 40° C. over 60 minutes. The obtained suspension was stirred at 40° C. for 5 h followed by cooling to 20° C. over 60 minutes. The suspension was stirred for 15 h at 20° C., and then filtered over a Büchner funnel under nitrogen. The wet product was suspended in n-heptane (2680 ml) and agitated at 20-25° C. for 30 min. The suspension was again filtered over a Büchner funnel under nitrogen and the wet product was dried at 40° C. under reduced pressure (20 mbars) until constant mass was obtained. The obtained material was analyzed by XRPD (Form II—FIG. 14), SSNMR and FTIR (FIGS. 5 and 6, accordingly).

Example 19: Preparation of Crystalline Trisodium Valsartan:Sacubitril Form II

In a 1 l jacketed glass reactor valsartan disodium trihydrate (24.00 g) and sacubitril sodium (19.50 g) were dissolved in toluene (875 ml) at reflux temperature. The solution was cooled down from reflux to 48° C. over 60 minutes. The suspension was stirred at 50° C. for 2 h at maximum dissipation energy of 0.7 W/kg followed by cooling to 20° C. over 35 minutes. The suspension was stirred at maximum dissipation energy of 0.7 W/kg for 1 h and then filtered over a Büchner funnel under nitrogen. The product was washed twice with methyl tert-butyl ether (175 ml). and dried at 25° C. under reduced pressure over 5 h (20 mbars) until constant mass was obtained. The obtained spherical material (see FIG. 7) was analyzed by XRPD-Form II.

Example 20: Preparation of Crystalline Trisodium Valsartan:Sacubitril Form II Sacubitril hemicalcium salt (5.00 g) was suspended in ethyl-acetate (210 mil) at room temperature. HCl (2M, 28.5M) was added and the mixture was agitated for 30 minutes. Layers were separated and the organic layer was washed with water. Valsartan acid (4.95 g) and sodium carbonate (1.78 gr) were added into the ethyl-acetate solution, heated to 40° C. and agitated for 60 min. The solvent was evaporated to dryness. 100 ml of toluene was added to the residue and the solvent was evaporated to dryness. Toluene (210 ml) was added to the residue and the mixture was heated to 80° C. Water (0.5 ml) was added and the mixture was cooled down to 50° C. and stirred for 2 h followed by cooling to 20° C. The suspension was stirred for 1 h at 20° C. and then filtered over a Büchner funnel. The wet product was suspended in n-heptane (60 ml) and agitated at 20-25° C. for 30 min. The suspension was again filtered over a Büchner funnel. The product was washed with n-heptane (30 ml) and dried at 25° C. under reduced pressure (20 mbars) until constant mass was obtained. Material was analyzed by XRPD-Form II.

Example 21: Preparation of Sacubitril Sodium

Figure 8:
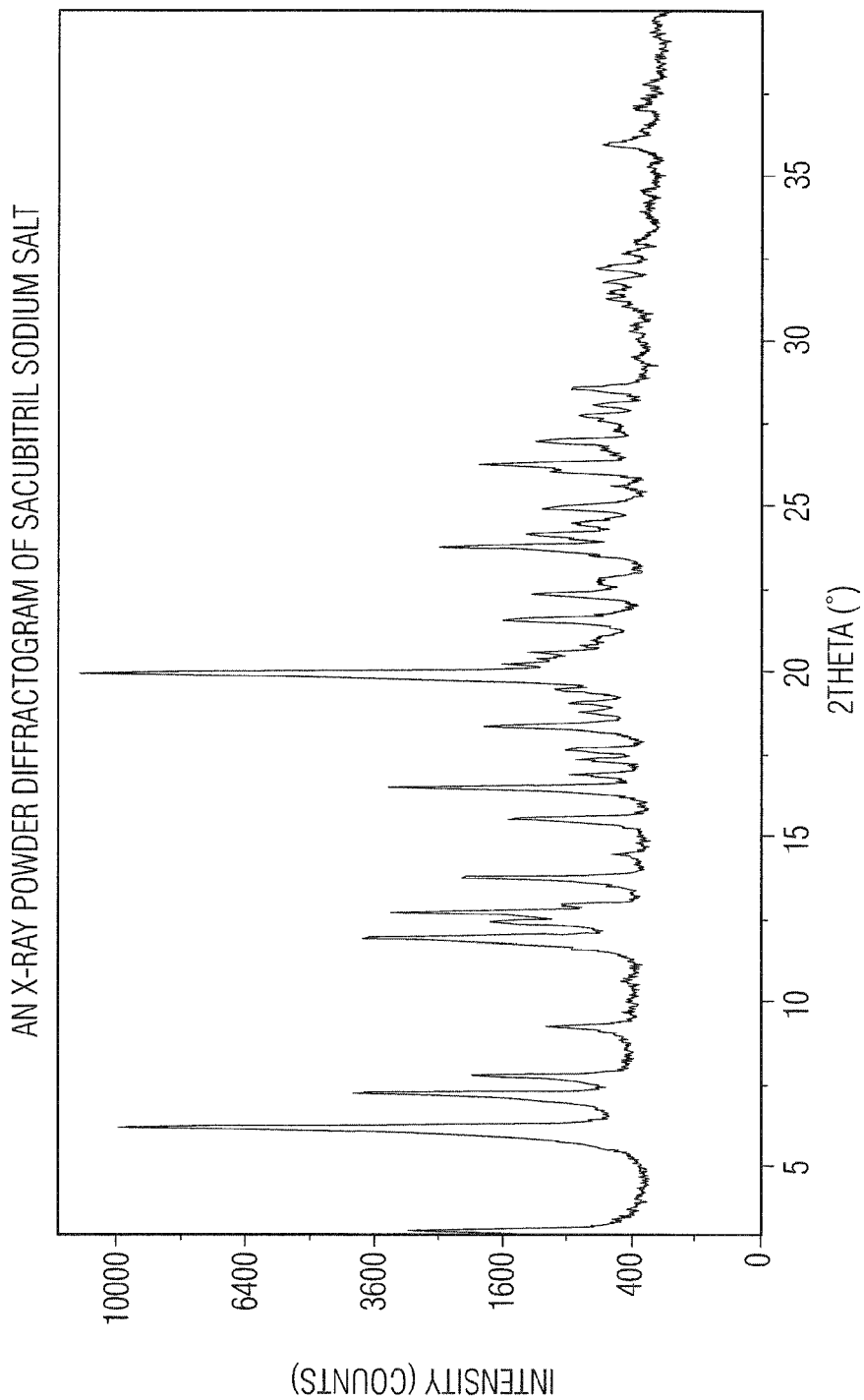
FIG. 8 shows an X-ray powder diffractogram of sacubitril sodium salt.

In a 1 l jacketed glass reactor, sacubitril hemicalcium salt (40 gr) was suspended in ethyl acetate (402 ml) at room temperature. HCl (2M, 58 ml) was added over 60 minutes. The mixture was agitated until dissolution and the layers were separated. The organic layer was washed with water (3*133 ml) and evaporated to dryness. The remaining residue was dissolved in acetonitrile (741 ml) and NaOH (10M, 6.9 ml) was added into the solution at room temperature. The suspension was stirred at 22° C. over 20 h. The suspension was filtered over a Büchner funnel under nitrogen and the product was washed with acetonitrile (1*200 ml). The wet product was dried at 35° C. under reduced pressure until constant mass was obtained. Material was analyzed by XRPD (FIG. 8).

Example 22: Preparation of Valsartan Disodium Trihydrate

Figure 9:
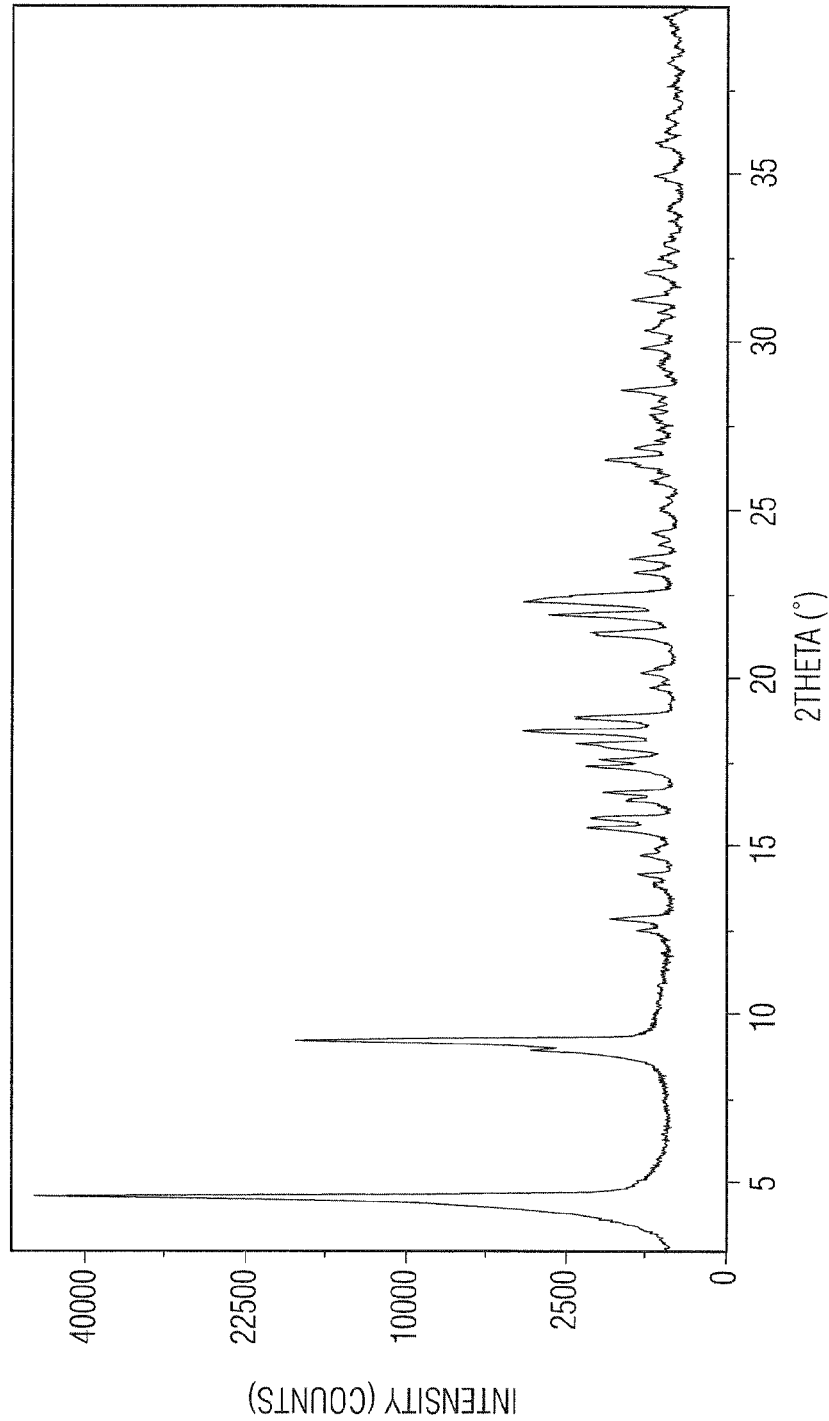
FIG. 9 shows an X-ray powder diffractogram of valsartan disodium salt.

In a 3 l jacketed glass reactor, valsartan add (300 g) was dissolved in acetone (1200 ml) at room temperature. Sodium carbonate (73.5 gr) and deionized water (60 ml) were added and heated up to reflux temperature. The mixture was agitated at reflux for 3 hours and afterwards cooled to room temperature. Methyl tert-butyl ether (MTBE) (1200 ml) was added and the mixture was stirred for 15 hours at 20° C. The suspension was filtered over a Büchner funnel and the wet product was washed with a mixture of acetone:MTBE (1:1, 300 ml). The wet product was dried at 35° C. under reduced pressure (20 mbars) until constant mass was obtained. Material was analyzed by XRPD (FIG. 9).

Example 23: Bulk Density and Tap Density of Form II

Samples of Form II were analyzed in the range of 10-20 g. Whole amount material was put in graduated cylinder. A graduated cylinder with the sample was attached to Erweka SVM tapped density tester and tapped with 1250 strikes. Volume of the powder is measured. Bulk density is measured as ratio between mass of sample (ms) and unsettled apparent volume (V0) of sample in graduated cylinder. Tap Density is measured as ratio between mass of sample (ms) and final tapped volume of sample (Vf). Compressibility index and Hausner ratio were calculated according to obtained results of bulk and tapped density. Form II according to the present invention has a Hausner ratio of 1.10-1.14, and a compressibility index of 10-12. The flow properties of Form II are characterized as good-excellent (according to Carr RL. Evaluating flow properties of solids. Chem Eng 1965; 72:163-168).

Example 24: SEM of Form II

Figure 7:
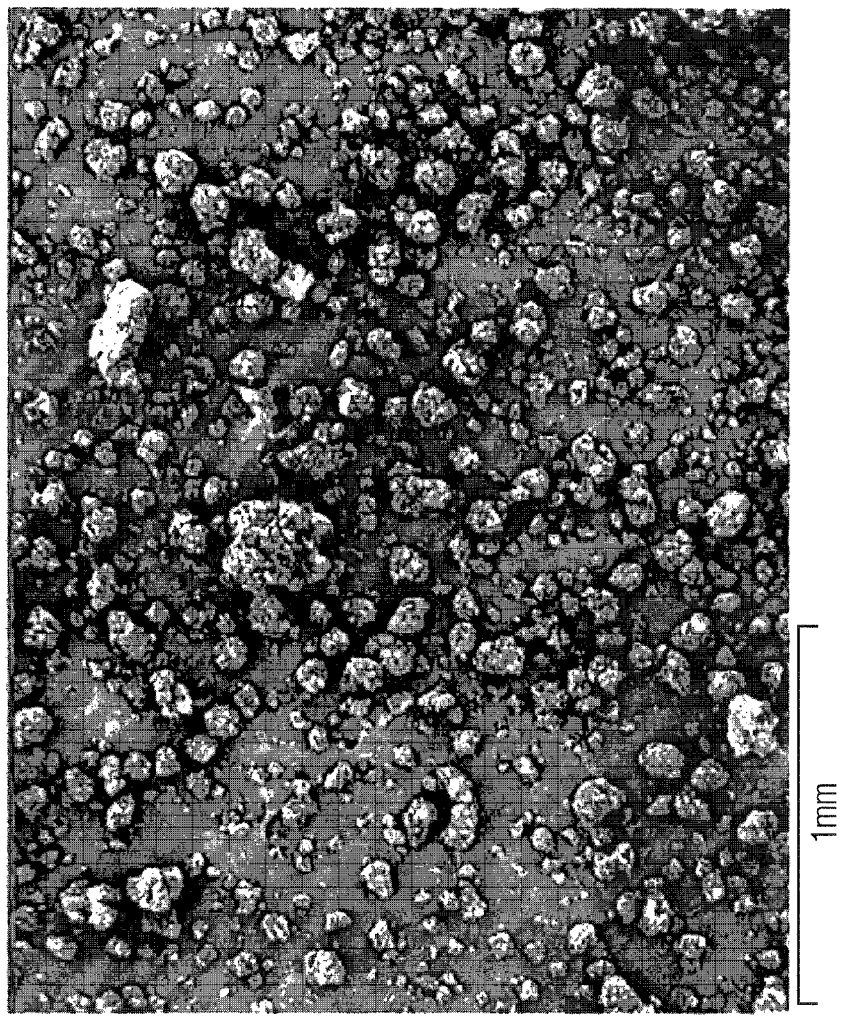
FIG. 7 shows SEM images of spherical particles of trisodium valsartan:sacubitril form II.

An SEM micrograph was taken on Joel JSM-5800 scanning microscope at 20 kV, WD 20-22, low current. Samples were sputtered with gold by Edwards S150 sputter coater (FIG. 7).

Example 25: Preparation of LCZ696 with Characteristic Peaks at 4.2, 5.0, 6.5 and 12.6 Degrees 2-Theta±0.2 Degrees 2-Theta Valsartan disodium trihydrate (100 mg) and sacubitril sodium (100 mg) was suspended in 2 ml of acetonitrile for 3 hours. The obtained product was analyzed by XRPD (FIG. 12).

Example 26: Preparation of LCZ696 with Characteristic Peaks at 4.2, 5.0, 6.5 and 12.6 Degrees 2-Theta±0.2 Degrees 2-Theta In a 1 1 glass jacketed reactor, 24.00 g of valsartan disodium trihydrate and 19.50 g of sacubitril sodium were suspended in 435 ml of acetonitrile. The mixture was agitated at 25° C. over 8 h. The suspension was filtered over a Büchner funnel and the wet cake was washed twice with 174 ml portions of MTBE. The wet product was dried at 25° C. under reduced pressure until constant mass was obtained. The obtained yield was 88.7%. Material was analyzed by XRPD and was found to correspond to FIG. 12.

Example 27: Preparation of LCZ696 with Characteristic Peaks at 4.2, 5.0, 6.5 and 12.6 Degrees 2-Theta±0.2 Degrees 2-Theta Valsartan disodium trihydrate (100 mg) and sacubitril sodium (100 mg) was suspended in 2 ml of acetone for 3 hours. The obtained product was analyzed by XRPD.

Example 28: Preparation of LCZ696 with Characteristic Peaks at 4.2, 5.0, 6.5 and 12.6 Degrees 2-Theta±0.2 Degrees 2-Theta Valsartan disodium trihydrate (100 mg) and sacubitril sodium (100 mg) was suspended in 2 ml of ethyl acetate for 3 hours. The obtained product was analyzed by XRPD.

Example 29: Preparation of LCZ696 with Characteristic Peaks at 4.2, 5.0, 6.5 and 12.6 Degrees 2-Theta±0.2 Degrees 2-Theta Valsartan disodium trihydrate (100 mg) and sacubitril sodium (100 mg) was suspended in 2 ml of i-propy acetate for 3 hours. The obtained product was analyzed by XRPD.

Example 30: Preparation of Crystalline Trisodium Valsartan:Sacubitril Form II 50 mg Trisodium Valsartan:Sacubitril cocrystal (LCZ696) is suspended in methyl benzoate (10 ml) and heated at 140-150° C. Solution was cooled down to room temperature and left to evaporate for 24 hours. Obtained product was analyzed by XRD and DSC.

Example 31: Preparation of Crystalline Trisodium Valsartan:Sacubitril Form

In a 6 l jacketed glass reactor, 100.0 g of sacubitril hemicalcium salt was suspended in 4150 ml of toluene at room temperature. 570 ml of 2M HCl was added and the mixture was agitated for 30 minutes. Layers were separated and the organic layer was washed once with 1000 ml of water. The mixture was heated to 40° C. 99.1 g of valsartan acid and 35.7 g of sodium carbonate were added and the mixture agitated for 90 min. The mixture was heated to reflux and water was removed out of the mixture by azeotropic distillation. The mixture was cooled to 80° C. followed by addition of 12.3 ml of water. The mixture was cooled down to 50° C. upon which precipitation occurred. The suspension was stirred at 50° C. for 3 hrs followed by cooling to 20° C. After a 2 h period of agitation at 20° C., the suspension was filtered over a 5 L filter dryer. The wet product was suspended in 1200 ml of n-heptane and agitated at 20-25° C. for 15 min. The cake wash was filtered off and the cake was washed again with 300 ml of n-heptane. The product was dried in the filter dryer at 40° C. and under reduced pressure until loss on drying result below 5.0%. 183.5 g of dry product was obtained.

Example 32: Morphology

Using the above-described method for determining morphology, crystalline Form II according to the invention (e.g. as prepared according to Example 19) was found to have circularity (v0.5) of greater than 0.85, i.e. 50% or greater of the agglomerates have a circularity of greater than 0.85.

Example 33: Thermogravimetric Analysis

Figure 13:
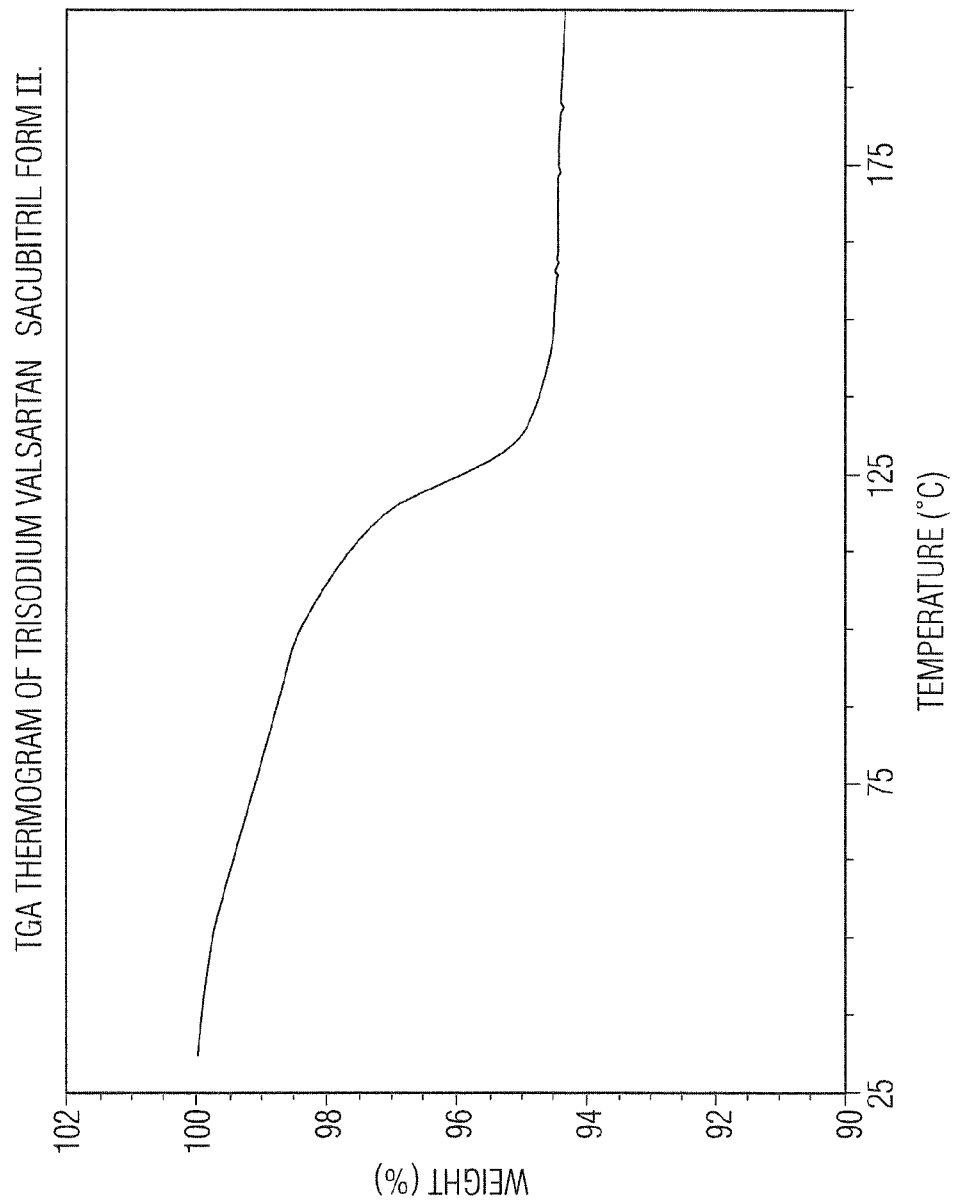
FIG. 13: TGA thermogram of trisodium valsartan:sacubitril form II.

Using the above-described method for TGA, the water content of the crystalline Form II of the present invention is in the range of 5.2 to 5.7 wt % (FIG. 13).

Example 34: Stability

Crystalline Form II of trisodium valsartan:sacubitril was found to be chemically and polymorphically stable when stored for 8 weeks at 25° C./60% RH, or at 50° C.

Crystalline Form II of trisodium valsartan:sacubitril was further found to be chemically and polymorphically stable when protected from moisture and stored under the following conditions:

25° C./60% RH
40° C./75% RH
50° C.
50° C./80% RH

Further aspects and embodiments of the present invention are provided in the following numbered Paragraphs:

1. Crystalline form II of trisodium valsartan:sacubitril characterized by data selected from one or more of the following:
   (i) an X-ray powder diffraction pattern having peaks at 5.8, 7.3, 12.9, 15.9, 16.5 and 18.6 degrees two theta±0.2 degrees two theta; and/or
   (ii) an X-ray powder diffraction pattern having peaks at: 7.3, 16.5, 9.4, 10.9 and 14.7 two theta±0.2 degrees two theta; and/or
   (iii) X-ray powder diffraction d-spacings at: 20.341, 15.261, 12.068, 9.397, 8.826, 8.092, 6.863, 6.024, 5.583, 5.353 and 4.773 Å±0.1 Å; and/or
   (iv) a solid state $^{13}$C NMR spectrum having peaks at 176.8, 161.9, 141.1, 139.5, 138.6, 137.2, 129.3, 128.7, 126.3, 124.9, 64.2, 60.6, 47.5, 46.1, 40.1, 39.0, 38.1, 34.3, 32.7, 29.8, 28.2, 22.4, 20.2, 17.8, 16.5, 13.7, 11.7 ppm±0.2 ppm.

2. A crystalline form II of trisodium valsartan:sacubitril according to Paragraph 1 characterized by data selected from one or more of the following:
   (i) an X-ray powder diffraction pattern having peaks at 5.8, 7.3, 12.9, 15.9, 16.5 and 18.6 degrees two theta±0.2 degrees two theta; and/or
   (ii) an X-ray powder diffraction pattern having peaks at: 7.3, 16.5, 9.4, 10.9 and 14.7 two theta±0.2 degrees two theta.

3. A crystalline form according to Paragraph 2, which is characterized by an X-ray powder diffraction pattern having peaks at 5.8, 7.3, 12.9, 15.9, 16.5 and 18.6 degrees two theta±0.2 degrees two theta and also having any one, any two, any three or more additional peaks selected from: 4.3, 9.4, 10.0, 10.9 and 14.7 two theta±0.2 degrees two theta.

4. A crystalline form according to Paragraph 2, which is characterized by the X-ray powder diffraction pattern having peaks at 7.3, 16.5, 9.4, 10.9 and 14.7 two theta±0.2 degrees two theta and also having any one, any two, any three or more additional peaks selected from: 4.3, 5.8, 10.0, 12.9, 15.9 and 18.6 two theta±0.2 degrees two theta and optionally further characterized by an FTIP spectrum as depicted in FIG. 6.

5. A crystalline form according to Paragraph 1 or Paragraph 2, which is characterized by the X-ray powder diffraction pattern having peaks at 4.3, 5.8, 7.3, 9.4, 10.0, 10.9, 12.9, 14.7, 15.9, 16.5, and 18.6 two theta±0.2 degrees two theta±0.2 degrees two theta.

6. A crystalline form according to Paragraph 5, which is further characterized by X-ray powder diffraction d-spacings at: 20.341, 15.261, 12.068, 9.397, 8.826, 8.092, 6.863, 6.024, 5.583, 5.353 and 4.773 Å±0.1 Å.

7. A crystalline form according to any of Paragraphs 1, 2, 3 or 4, further characterized by an X-ray powder diffraction pattern having one, two, three, four five, or more than 5 additional peaks selected from: 4.3, 5.0, 5.5, 5.8, 7.3, 8.5, 8.9, 9.4, 10.0, 10.9, 11.6, 12.9, 13.7, 13.9, 14.7, 14.8, 15.1, 15.3, 15.9, 16.5, 17.3, 17.6, 18.6, 19.1, 19.5, 20.3, 21.2, 21.9 and 23.1 degrees two theta±0.2 degrees two theta.

8. A crystalline form according to any of Paragraphs 1, 2, 3, 4, 5, 6 or 7, which is characterized by an X-ray powder diffraction pattern having peaks at: 4.3, 5.0, 5.5, 5.8, 7.3, 8.5, 8.9, 9.4, 10.0, 10.9, 11.6, 12.9, 13.7, 13.9, 14.7, 14.8, 15.1, 15.3, 15.9, 16.5, 17.3, 17.6, 18.6, 19.1, 19.5, 20.3, 21.2, 21.9 and 23.1 degrees two theta±0.2 degrees two theta.

9. A crystalline form according to Paragraph 8, which is further characterized by the absence of any peak (defined as relative intensity I/Io of less than 1%) between any of two neighboring peaks.

10. A crystalline form according to any of Paragraphs 1, 2, 3, 4, 5, 6, 7, 8 or 9, further characterized by an X-ray powder diffraction pattern as depicted in FIG. 1 or FIG. 14 and/or a solid state $^{13}$C NMR as depicted in FIG. 5.
11. A crystalline form according to any of Paragraphs 1, 2, 3, 4, 5, 6, 7, 8, 9 or 10, further characterized by a DSC as depicted in FIG. 2.
12. A crystalline form according to any of Paragraphs 2-11 further characterized by a solid state $^{13}$C NMR spectrum having peaks at 176.8, 161.9, 141.1, 139.5, 138.6, 137.2, 129.3, 128.7, 126.3, 124.9, 64.2, 60.6, 47.5, 46.1, 40.1, 39.0, 38.1, 34.3, 32.7, 29.8, 28.2, 22.4, 20.2, 17.8, 16.5, 13.7, 11.7 ppm±0.2 ppm.
13. A crystalline form according to any of Paragraphs 1, 2, 3, 4, 5, 6, 7, 8, 9, 10, 11 or 12, which is substantially free of any other forms of trisodium valsartan:sacubitril.
14. A crystalline form according to any of Paragraphs 1, 2, 3, 4, 5, 6, 7, 8, 9, 10, 11, 12 or 13, which contains: 20% (w/w) or less, 10% (w/w) or less; or 5% (w/w) or less; or 2% (w/w) or less of polymorphs, or of a specified polymorph of trisodium valsartan:sacubitril.
15. A crystalline form according to any of Paragraphs 1, 2, 3, 4, 5, 6, 7, 8, 9, 10, 11, 12, 13 or 14, which contains: from 2% to 20% (w/w); from 5% to 20% (w/w); or from 5% to 10% (w/w) of one or more solid state forms or one or more polymorphs of trisodium valsartan:sacubitril which is/are different from the predominant solid state of trisodium valsartan:sacubitril which is present.
16. A crystalline form according to any of Paragraphs 1, 2, 3, 4, 5, 6, 7, 8, 9, 10, 11, 12, 13, 14 or 15, which is a hydrate, preferably wherein the crystalline form contains from 5.2 to 5.7 wt % water.
17. A crystalline form according to any of Paragraphs 1, 2, 3, 4, 5, 6, 7, 8, 9, 10, 11, 12, 13, 14, 15 or 16, comprising agglomerates having spherical morphology, preferably wherein: at least 50%, at least 60%, at least 70%, at least 80% or at least 90% of the agglomerates have spherical morphology, preferably wherein the circularity of at least 50% (preferably: at least 60%, at least 70%, at least 80% or at least 90%) of the particles on a volume basis is: greater than or equal to about 0.85, about 0.86 to 1, about 0.88 to about 0.98, about 0.90 to about 0.96, about 0.92 to about 0.96.
18. A process for preparing a crystalline form II of trisodium valsartan:sacubitril comprising:
    (i) combining trisodium valsartan:sacubitril with a solvent and heating to form a solution, preferably wherein the solvent comprises an aromatic solvent, preferably toluene and/or methyl benzoate
    (ii) cooling the solution to obtain a mixture, and
    (iii) isolating the crystalline form from the mixture, preferably wherein the trisodium valsartan sacubitril is a hydrate form.
19. A process for preparing a crystalline form II of trisodium valsartan:sacubitril comprising:
    (i) combining disodium valsartan and sacubitril sodium with a solvent to form a solution, preferably wherein the solvent comprises toluene,
    (ii) cooling and/or removing at least a portion of the solvent to obtain a mixture, and
    (iii) isolating the crystalline form from the mixture, preferably wherein the disodium valsartan is a hydrate form.
20. A process according to any of Paragraphs 18 or 19, wherein the solution in step (i) is prepared by heating, preferably to a temperature of about 80° C. to about 150° C., about 90° C. to about 130° C.
21. A process according to any of Paragraphs 18, 19 or 20, wherein step ii) comprises cooling to a temperature of about 4-28° C., preferably about 5 to about 25° C. and more preferably about 5 to about 20° C.
22. A process according to any of Paragraphs 18, 19, 20 or 21, wherein step (iii) comprises filtering the mixture from step (ii), and exposing the resulting solid to a relative humidity of about 40 to 80%, preferably 50 to 70% and more preferably about 60%.
23. A process according to any of Paragraphs 19, 20 or 21, wherein the disodium valsartan is in the form of a hydrate, preferably a trihydrate.
24. A process according to Paragraph 23, wherein step (iii) comprises filtering the mixture obtained in step (ii), slurrying the solid in a solvent comprising a $C_6$-$C_{10}$ alkane, preferably n-heptane, and isolating the crystalline form.
25. A process for preparing a crystalline form II of trisodium valsartan:sacubitril comprising:
    (i) providing a solution of sacubitril in a solvent, preferably wherein the solvent is water immiscible, more preferably wherein the solvent comprises ethyl acetate and/or toluene, and most preferably wherein the solvent is ethyl acetate or toluene,
    (ii) adding valsartan acid and a sodium base, preferably sodium carbonate or sodium hydroxide, and more preferably in a molar equivalent of about 2.8 to about 3.2 moles of sodium per mole of valsartan or sacubitril, to the sacubitril solution, and
    (iii) isolating the crystalline form.
26. A process according to Paragraph 25, wherein after adding the valsartan acid and sodium base and prior to isolating the crystalline form, the following steps are carried out:
    (ii-a) optionally removing the solvent,
    (ii-b) optionally adding toluene and water to form a mixture,
    (ii-c) optionally heating the mixture, and
    (ii-d) cooling the mixture.
27. A process according to Paragraph 25 or Paragraph 26, wherein step (iii) comprises filtering the mixture from step (ii-b) or (ii-d), suspending the resulting solid in a solvent, preferably wherein the solvent comprises a $C_6$-$C_{10}$ alkane, preferably heptane, and filtering.
28. A process according to any of Paragraphs 25, 26 or 27, wherein the solution of sacubitril in a solvent is prepared by combining an alkali or alkali earth metal salt of sacubitril (preferably sacubitril hemicalcium salt), optionally in the form of a hydrate, in the solvent (preferably wherein the solvent comprises ethyl acetate or toluene), and acidifying with an aqueous mineral acid, preferably hydrochloric acid, and removing the aqueous layer.
29. A process according to Paragraph 28, wherein crystallization of form II is conducted in the presence of water, preferably wherein water is present in an amount of about 94 to about 138 ml of water per kg of sacubitril alkali or alkali earth metal salt (preferably relative to sacubitril hemicalcium salt in anhydrous form), more preferably about 120 to about 130 ml of water per kg of sacubitril alkali or alkali earth metal salt (preferably sacubitril hemicalcium salt).
30. A process for preparing a crystalline form II of trisodium valsartan:sacubitril comprising:
    (i) combining valsartan acid and sacubitril acid with an organic solvent, preferably wherein the solvent comprises ethyl acetate, (ii) adding aqueous sodium hydroxide, preferably in a molar equivalent amount of 3.0-3.1 per mole of valsartan acid or relative to sacubitril acid, to form a mixture, and (iii) isolating the crystalline form.

31. A process according to Paragraph 30, wherein after adding the aqueous sodium hydroxide, and prior to isolating the crystalline form, the following steps are carried out:

(ii-a) optionally removing a portion of the solvent, (ii-b) adding an organic solvent, preferably comprising toluene to the mixture, (ii-c) optionally concentrating the mixture, (ii-d) optionally repeating step (ii-b), (ii-e) heating the mixture, (ii-f) cooling the mixture, and (ii-g) filtering the resulting solid and subjecting the solid to a relative humidity of about 40 to 80%, preferably 50 to 70% and more preferably about 60%.

32. A process according to any of Paragraphs 18, 19, 20, 21, 22, 23, 24, 25, 26, 27, 28, 29, 30 or 31, wherein during and/or after (preferably after) the step of cooling the mixture, the mixture is agitated, preferably wherein the agitation is at a dissipation energy of ≤2.0 W/kg, more preferably at a dissipation energy of 0.2 to 2.0 W/kg, more preferably at a dissipation energy of 0.5 to 1.5 W/kg, and most preferably at a dissipation energy of 0.5 to 1.0 W/kg, preferably wherein the dissipation energy is set to a lower value of 1.7 W/kg after crystallization occurs, wherein the agitation is preferably carried out at a temperature of 45-55° C.

33. A process according to Paragraph 32 wherein the mixture is agitated for: about 0.1 to about 5 hours, about 0.25 to about 4 hours, or about 1 to about 3 hours.

34. A process for preparing a crystalline form II of trisodium valsartan:sacubitril comprising homogenizing a mixture of valsartan acid, sacubitril sodium and sodium hydroxide, preferably in a molar equivalent amount of 2.0-2.1 per mole of valsartan acid, in a solvent to form a mixture, preferably wherein the solvent comprises toluene.

35. A process for preparing a crystalline form II of trisodium valsartan:sacubitril comprising suspending a mixture of valsartan disodium (preferably in hydrated form) and sacubitril sodium in a solvent, preferably wherein the solvent comprises toluene and/or 2-methyl tetrahydrofuran.

36. A process according to Paragraph 35, wherein the suspending is carried out for about 0.5 to about 12 hours, more preferably for about 1 to about 8 hours, and particularly for about 2 to about 5 hours.

37. A process for preparing a crystalline form II of trisodium valsartan:sacubitril comprising contacting trisodium valsartan:sacubitril, preferably in amorphous form with a solvent comprising at least one of t-butyl methyl ether, 2-methyl tetrahydrofuran, or an aromatic solvent, preferably toluene or methyl benzoate, wherein the contacting is preferably at room temperature.

38. A process according to Paragraph 37, wherein the contacting comprises exposing the amorphous trisodium valsartan:sacubitril to vapours of the solvent, preferably for about 2 to about 14 days, more preferably for about 3-10 days, and particularly for about 5-8 days.

39. A process according to Paragraph 37, wherein the contacting comprises slurrying the amorphous trisodium valsartan:sacubitril in the solvent, preferably for about 0.5 to about 12 hours, more preferably for about 2 to about 8 hours, and particularly for about 2 to about 6 hours, and optionally isolating the crystalline form.

40. A process for preparing crystalline trisodium valsartan:sacubutril form II in a solvent comprising combining trisodium valsartan:sacubril (preferably in hydrated form) with an aromatic solvent, preferably wherein the aromatic solvent is selected from chlorobenzene, fluorobenzene, m-xylene, o-xylene, p-xylene, anisole and methyl benzoate, and most preferably methyl benzoate, heating the mixture to form a solution, cooling the solution, and optionally isolating the form II.

41. A process according to Paragraph 40 wherein prior to isolating the form II, the cooled solution is allowed to evaporate.

42. A process according to any of Paragraphs 18, 19, 20, 21, 22, 23, 24, 25, 26, 27, 28, 29, 30, 31, 32, 33, 34, 35, 36, 37, 38, 39, 40 or 41, further comprising drying the crystalline form optionally under reduced pressure and optionally with heating.

43. A process according to any of Paragraphs 18, 19, 20, 21, 22, 23, 24, 25, 26, 27, 28, 29, 30, 31, 32, 33, 34, 35, 36, 37, 38, 39, 40, 41 or 42, further comprising combining the crystalline form with at least one pharmaceutically acceptable excipient to form a pharmaceutical composition.

44. A crystalline form II of trisodium valsartan:sacubitril obtainable by a process according to any of Paragraphs 18, 19, 20, 21, 22, 23, 24, 25, 26, 27, 28, 29, 30, 31, 32, 33, 34, 35, 36, 37, 38, 39, 40, 41 or 42.

45. A crystalline form II of trisodium valsartan:sacubitril according to Paragraph 44, which is defined according to any of Paragraphs 1, 2, 3, 4, 5, 6, 7, 8, 9, 10, 11, 12, 13, 14, 15, 16 or 17.

46. A crystalline form II according to any of Paragraphs 1, 2, 3, 4, 5, 6, 7, 8, 9, 10, 11, 12, 13, 14, 15, 16, 17, 44 or 45 for use as a medicament.

47. A crystalline form according to any of Paragraphs 1, 2, 3, 4, 5, 6, 7, 8, 9, 10, 11, 12, 13, 14, 15, 16, 17, 44, 45 or 46, for use in the treatment of hypertension and heart failure.

48. Use of a crystalline form according to any of Paragraphs 1, 2, 3, 4, 5, 6, 7, 8, 9, 10, 11, 12, 13, 14, 15, 16, 17, 44 or 45, for the preparation of other solid state forms of trisodium valsartan:sacubitril, for the preparation of solid state forms of valsartan:sacubitril, or for the preparation of other salts of valsartan:sacubitril and their solid state forms, 49. Use of a crystalline form according to any of Paragraphs 1, 2, 3, 4, 5, 6, 7, 8, 9, 10, 11, 12, 13, 14, 15, 16, 17, 44 or 45, for the chemical purification of valsartan:sacubitril and salts thereof.

50. Use according to Paragraph 49, wherein the chemical purification comprises crystallizing form II of trisodium valsartan:sacubitril, preferably comprising crystallizing trisodium valsartan:sacubitril from toluene.

51. Use of a crystalline form according to any of Paragraphs 1, 2, 3, 4, 5, 6, 7, 8, 9, 10, 11, 12, 13, 14, 15, 16, 17, 44 or 45, for the preparation of pharmaceutical compositions and/or formulations of valsartan:sacubitril.

52. A pharmaceutical composition or formulation comprising a crystalline form according to any of Paragraphs 1, 2, 3, 4, 5, 6, 7, 8, 9, 10, 11, 12, 13, 14, 15, 16, 17, 44 or 45, preferably wherein the pharmaceutical composition is a solid composition and the trisodium valsartan:sacubitril retains its solid state form.

53. A pharmaceutical composition or formulation comprising a crystalline form according to any of Paragraphs 1, 2, 3, 4, 5, 6, 7, 8, 9, 10, 11, 12, 13, 14, 15, 16, 17, 44 or 45 and a pharmaceutically acceptable excipient.

54. A process for preparing a pharmaceutical composition or formulation according Paragraph 52 or 53, comprising combining a crystalline form according to any of Paragraphs 1, 2, 3, 4, 5, 6, 7, 8, 9, 10, 11, 12, 13, 14, 15, 16, 17, 44 or 45 with at least one pharmaceutically acceptable excipient.

55. A method of treating hypertension or heart failure, comprising administration of an effective amount of a pharmaceutical composition comprising a crystalline form of trisodium valsartan:sacubitril according to any of Paragraphs 1, 2, 3, 4, 5, 6, 7, 8, 9, 10, 11, 12, 13, 14, 15, 16, 17, 44 or 45 to a subject in need thereof.

56. A process for preparing a crystalline form of trisodium valsartan:sacubitril (preferably in hydrated form), wherein the crystalline form is characterized by data selected from:
   (i) an X-ray powder diffraction pattern having peaks at 4.2, 5.0, 6.5 and 12.6 degrees two theta±0.2 degrees two theta; and optionally, one, two three or four additional peaks at 6.2 13.7, 14.9 and 15.4 degrees two theta±0.2 degrees two theta; or
   (ii) an X-ray powder diffraction pattern having peaks at 4.2, 5.0, 6.5 and 12.6 degrees two theta±0.2 degrees two theta; and additional peaks at 6.2 13.7, 14.9 and 15.4 degrees two theta±0.2 degrees two theta; or
   (iii) an X-ray powder diffraction pattern substantially as depicted in FIG. 12, wherein the process comprises crystallising trisodium valsartan:sacubitril (preferably in hydrated form) from a solvent comprising acetonitrile, acetone, ethyl acetate or isopropyl acetate or a combination thereof.

57. A process according to Paragraph 56, wherein the process comprises:
   (a) suspending valsartan disodium trihydrate and sacubitril sodium in a solvent comprising acetonitrile, ethyl acetate, or isopropyl acetate, optionally with stirring, and
   (b) optionally isolating the crystalline form.

58. A process according to Paragraph 56 or Paragraph 57, wherein the solvent in step (a) is acetonitrile.

59. A process according to any of Paragraphs 56, 57 or 58, wherein step (a) is carried out for a period of from about 1 to about 18 hours, preferably from about 1 to about 12 hours, more preferably from about 2 to about 10 hours.

60. A process according to any of Paragraphs 56, 57, 58 or 59, wherein step (a) is carried out at a temperature of about 15 to about 40° C., preferably about 20 to about 30° C.

61. A process according to any of Paragraphs 56, 57, 58, 59 or 60, wherein step (b) comprises filtering the solid and optionally drying the product, wherein the drying is preferably conducted at a temperature of about 15 to about 40° C., preferably about 20 to about 30° C.

62. A process according to any of Paragraphs 56, 57, 58, 59, 60 or 61, further comprising combining the crystalline form with at least one pharmaceutically acceptable excipient to form a pharmaceutical composition.

63. A crystalline form of trisodium valsartan:sacubitril in hydrate form or a pharmaceutical composition thereof, obtainable by a process according to any of Paragraphs 56, 57, 58, 59, 60, 61 or 62.

The invention claimed is:
1. Crystalline form II of trisodium valsartan: sacubitril characterized by an X-ray powder diffraction pattern having peaks at: 7.3, 16.5, 9.4, 10.9 and 14.7 degrees two theta±0.2 degrees two theta, and an absence of a peak at 12.4 degrees two theta±0.2 degrees two theta.

2. A crystalline form according to claim 1, which is characterized by an X-ray powder diffraction pattern as depicted in FIG. 1.

3. A crystalline form according to claim 1, which is characterized by the X-ray powder diffraction pattern having additional peaks at: 4.3, 5.8, 10.0, 12.9, 15.9 and 18.6 two theta±0.2 degrees two theta.

4. A crystalline form according to claim 1, which is further characterized by the X-ray powder diffraction pattern having peaks at 4.3, 5.8, 7.3, 9.4, 10.0, 10.9, 12.9, 14.7, 15.9, 16.5, and 18.6 two theta±0.2 degrees two theta±0.2 degrees two theta.

5. A crystalline form according to claim 1, further characterized by an X-ray powder diffraction pattern having peaks at: 4.3, 5.0, 5.5, 5.8, 7.3, 8.5, 8.9, 9.4, 10.0, 10.9, 11.6, 12.9, 13.7, 13.9, 14.7, 14.8, 15.1, 15.3, 15.9, 16.5, 17.3, 17.6, 18.6, 19.1, 19.5, 20.3, 21.2, 21.9 and 23.1 degrees two theta±0.2 degrees two theta.

6. A crystalline form according to claim 1, wherein the crystalline form contains from 5.2 to 5.7 wt % water.

7. A crystalline form according to claim 1, comprising agglomerates having spherical morphology, wherein at least 50% of the agglomerates have spherical morphology.

8. A crystalline form according to claim 1, further characterized by a solid state $^{13}$C NMR spectrum having peaks at 176.8, 161.9, 141.1, 139.5, 138.6, 137.2, 129.3, 128.7, 126.3, 124.9, 64.2, 60.6, 47.5, 46.1, 40.1, 39.0, 38.1, 34.3, 32.7, 29.8, 28.2, 22.4, 20.2, 17.8, 16.5, 13.7, 11.7 ppm±0.2 ppm.

9. A crystalline form according to claim 1, which contains 20% (w/w) or less of a trisodium valsartan: sacubitril polymorph that is different from crystalline form II.

10. A crystalline form according to claim 1, which contains 10% (w/w) or less of a trisodium valsartan: sacubitril polymorph that is different from crystalline form II.

11. A crystalline form according to claim 1, which contains 5% (w/w) or less of a trisodium valsartan: sacubitril polymorph that is different from crystalline form II.

12. A crystalline form according to claim 1, further characterized by X-ray powder diffraction d-spacings at: 20.341, 15.261, 12.068, 9.397, 8.826, 8.092, 6.863, 6.024, 5.583, 5.353 and 4.773 Å±0.1 Å.

13. A pharmaceutical composition or formulation comprising a crystalline form II of trisodium valsartan: sacubitril as defined in claim 1 and at least one pharmaceutically acceptable excipient.

14. A process for preparing a pharmaceutical composition or formulation according claim 13 comprising combining form II of trisodium valsartan: sacubitril with at least one pharmaceutically acceptable excipient.

15. A method of treating hypertension or heart failure in a subject in need thereof, the method comprising the step of administering to the subject a therapeutically effective amount of trisodium valsartan: sacubitril form II as defined in claim 1; or a pharmaceutical formulation comprising the therapeutically amount of trisodium valsartan: sacubitril form II as defined in claim 1 and at least one pharmaceutically acceptable excipient.

16. A process for preparing a crystalline form II of trisodium valsartan: sacubitril comprising:
   combining trisodium valsartan: sacubitril with an aromatic solvent and heating to about 80° C. to about 150° C. to form a solution, wherein the aromatic solvent is toluene, chlorobenzene, fluorobenzene, m-xylene, o-xylene, p-xylene, anisole, or methyl benzoate;

cooling the solution to about 4° C. to about 28° C. to form a mixture; and isolating the crystalline form from the mixture;

wherein the crystalline form II of trisodium valsartan: sacubitril is characterized by an X-ray powder diffraction pattern having peaks at: 7.3, 16.5, 9.4, 10.9 and 14.7 degrees two theta±0.2 degrees two theta, and an absence of a peak at 12.4 degrees two theta±0.2 degrees two theta.

17. A process for preparing a crystalline form II of trisodium valsartan: sacubitril comprising:

combining disodium valsartan and sacubitril sodium with an aromatic solvent and heating to about 80° C. to about 150° C. to form a solution, wherein the aromatic solvent is toluene, chlorobenzene, fluorobenzene, m-xylene, o-xylene, p-xylene, anisole, or methyl benzoate;

cooling the solution to about 4° C. to about 28° C. and/or removing at least a portion of the solvent to obtain a mixture, and isolating the crystalline form from the mixture;

wherein the crystalline form II of trisodium valsartan: sacubitril is characterized by an X-ray powder diffraction pattern having peaks at: 7.3, 16.5, 9.4, 10.9 and 14.7 degrees two theta±0.2 degrees two theta, and an absence of a peak at 12.4 degrees two theta±0.2 degrees two theta.

18. The process of claim 17, wherein the solvent is toluene.

19. A process for preparing a crystalline form II of trisodium valsartan: sacubitril comprising:

providing a solution of sacubitril in a solvent that is ethyl acetate and/or toluene, optionally wherein the solution of sacubitril in a solvent is prepared by combining an alkali or alkali earth metal salt of sacubitril in the solvent and acidifying with an aqueous mineral acid;

adding valsartan acid and a sodium base to the solution to form a mixture;

optionally removing the solvent and adding toluene and water to form the mixture, heating the mixture up to 80° C. and then cooling the mixture to about 20° C.; and isolating the crystalline form;

wherein the crystalline form II of trisodium valsartan: sacubitril is characterized by an X-ray powder diffraction pattern having peaks at: 7.3, 16.5, 9.4, 10.9 and 14.7 degrees two theta±0.2 degrees two theta, and an absence of a peak at 12.4 degrees two theta±0.2 degrees two theta.

20. A crystalline form II of trisodium valsartan: sacubitril obtainable by a process according to claim 16.

21. A crystalline form II of trisodium valsartan: sacubitril obtainable by a process according to claim 17.

22. A crystalline form II of trisodium valsartan: sacubitril obtainable by a process according to claim 19.

* * * * *